US007372941B2

(12) United States Patent
Ivanisevic et al.

(10) Patent No.: US 7,372,941 B2
(45) Date of Patent: May 13, 2008

(54) SYSTEM AND METHOD FOR MATCHING DIFFRACTION PATTERNS

(75) Inventors: Igor Ivanisevic, West Lafayette, IN (US); Simon Bates, West Lafayette, IN (US); David E. Bugay, West Lafayette, IN (US); Barbara C. Stahly, West Lafayette, IN (US); Donald R. Hallenbeck, West Lafayette, IN (US)

(73) Assignee: SSCI, Inc., West Lafayette, IN (US)

( * ) Notice: Subject to any disclaimer, the term of this patent is extended or adjusted under 35 U.S.C. 154(b) by 494 days.

(21) Appl. No.: 10/635,113

(22) Filed: Aug. 6, 2003

(65) Prior Publication Data

US 2004/0103130 A1 May 27, 2004

Related U.S. Application Data

(60) Provisional application No. 60/401,811, filed on Aug. 6, 2002.

(51) Int. Cl.
*G01N 23/20* (2006.01)
(52) U.S. Cl. ...................................... 378/70
(58) Field of Classification Search ............. 378/70, 378/71, 73
See application file for complete search history.

(56) References Cited

U.S. PATENT DOCUMENTS

| 5,870,697 | A | * | 2/1999 | Chandler et al. ........... 702/179 |
| 5,985,356 | A | | 11/1999 | Schultz et al. ................ 427/8 |
| 6,004,617 | A | | 12/1999 | Schultz et al. ................ 427/8 |
| 6,034,775 | A | | 3/2000 | McFarland et al. ......... 356/364 |
| 6,045,671 | A | | 4/2000 | Wu et al. .............. 204/298.11 |
| 6,157,449 | A | | 12/2000 | Hajduk ...................... 356/367 |
| 6,327,334 | B1 | * | 12/2001 | Murray et al. ................ 378/75 |
| 6,346,290 | B1 | | 2/2002 | Schultz et al. ................ 427/8 |
| 6,371,640 | B1 | | 4/2002 | Hajduk et al. ............. 378/208 |
| 6,459,763 | B1 | * | 10/2002 | Koinuma et al. ............. 378/71 |
| 6,489,168 | B1 | | 12/2002 | Wang et al. .................. 436/37 |
| 6,507,636 | B1 | * | 1/2003 | Lehmann ..................... 378/79 |
| 6,507,945 | B1 | | 1/2003 | Rust et al. .................. 717/103 |

(Continued)

FOREIGN PATENT DOCUMENTS

EP 1 103 806 A2 5/2001

(Continued)

OTHER PUBLICATIONS

B. D. Cillity and S. R. Stock, Elements of X-Ray Diffraction, third edition (New Jersey: Prentice Hall, 2001).*

(Continued)

*Primary Examiner*—Allen C. Ho
(74) *Attorney, Agent, or Firm*—Finnegan, Henderson, Farabow, Garrett & Dunner, LLP

(57) ABSTRACT

A method of analyzing patterns. The method comprises: receiving a first diffraction pattern; receiving a second diffraction pattern; receiving a third diffraction pattern; determining a similarity between the first and second diffraction patterns; determining a similarity between the first and third diffraction pattern; determining a similarity between the second and third diffraction pattern; and performing hierarchical cluster analysis on the first and second diffraction pattern based on the determined similarity.

14 Claims, 31 Drawing Sheets

U.S. PATENT DOCUMENTS

| | | | |
|---|---|---|---|
| 6,836,532 B2 * | 12/2004 | Durst et al. | 378/73 |
| 2002/0067800 A1 * | 6/2002 | Newman et al. | 378/73 |
| 2006/0015265 A1 * | 1/2006 | Raich | 702/22 |

FOREIGN PATENT DOCUMENTS

| | | | |
|---|---|---|---|
| EP | 1 080 435 B1 | 2/2002 | |
| WO | WO 01/79949 A2 | 10/2001 | |
| WO | WO 02/054188 A2 | 7/2002 | |

OTHER PUBLICATIONS

Vidal et al., "Multivariate cluster analysis of trace elements and mineralogical components from some rural soils," Development and Application of Computer Techniques to Environmental Studies VI, Proceedings of Sixth International Conference ENVIROSOFT 1996, p. 215-224.*

Infometrix, Inc., "Description of Pirouette Algortithms," Chemometrics Technical Note, 1993, p. 1-4.*

Igor Ivanisevic, David E. Bugay, and Simon Bates., J. Phys. Chem. B 109, 7781-7787 (2005).*

Toshiyuki Mitsui, Syuji Okuyama, and Yoshikazu Fujimura, Analytical Sciences, vol. 7, Dec. 1991, 941-945.*

Analytical Sciences, Japan Society For Analytical Chemistry, Tokyo, JP, vol. 7, Dec. 1991., "*Determination of the Blend Composition Ratio of Cocaine to Sodium Hydrogencarbonate by X-Ray Diffraction Using Multivariate Analysis*", Mitsui, et al., pp. 941-945.

Parallel Computing, Elsevier Publishers, Amsterdam, NL, vol. 21 No. 8, Aug. 1, 1995 "*Parallel algorithms for hierarchical clustering*", Olson, C.F., pp. 1313-1325.

Trac, Trends in Analytical Chemistry, Analytical Chemistry, Cambridge, GB, vol. 9, No. 9, Oct. 1990, "*Principal components regression in practice An evaluation of EMD battery activity from X-ray diffraction patterns*", Williams et al., pp. 303-308.

International Search Report mailed Dec. 16, 2003 for International Application No. PCT / US 03 / 24507.

R. De Gelder et al., "A Generalized Expression for the Similarity of Spectra: Application to Powder Diffraction Pattern Classification," Journal of Computational Chemistry, vol. 22, No. 3, pp. 273-289, 2001.

* cited by examiner

310

SYSTEM AND METHOD FOR MATCHING DIFFRACTION PATTERNS

RELATED APPLICATIONS

This application claims priority from U.S. Provisional Patent Application No. 60/401,811, filed Aug. 6, 2002, which is incorporated herein by reference.

TECHNICAL FIELD

The invention relates to the field of pattern matching, and more specifically, a system for and method of matching diffraction patterns utilizing hierarchical cluster analysis.

BACKGROUND

Diffraction is frequently used as an analytical technique to characterize compounds or elements. There are situations where a number of materials are analyzed by diffraction techniques and compared to one another in order to determine whether differences in the materials exist. For example, production lots of a compound might be analyzed by diffraction to ensure that the desired material is produced. As another example, a compound might be crystallized under a variety of conditions and the resulting solids analyzed by diffraction to determine if variations in solid form are present. As a third example, an ionizable compound might be reacted with a number of different counterions in an effort to generate a group of different salts. In this case, the solids from the reactions could be analyzed by diffraction and compared to diffraction analyses of the original material and the counterion to help determine whether a salt was formed. It would be useful to have a tool to quickly, easily, and accurately compare diffraction patterns of different materials and sort them into groups of similar patterns.

Hierarchical Cluster Analysis is a statistical method of pattern recognition with wide applicability. Whenever the application is to cluster relatively similar objects together into different groups, then HCA is a common method of choice. The core requirement of HCA is the derivation of a measure of similarity between the objects being clustered. The success of the HCA approach is dependent on the robustness of the measure of similarity chosen. The early implementations of HCA were statistical data analysis where the measure of similarity was the numerical equivalency of the results being analyzed. This has seen wide application for statistical quantitative analysis.

The use of HCA for clustering objects more complex than quantitative values has been limited by the availability of a suitable measure of similarity between the objects to be clustered. The appropriate choice of a measure of similarity is not obvious.

The present invention is directed to overcoming one or more of the above problems and achieving one or more of the above stated goals.

SUMMARY

Consistent with the present invention, a method of analyzing patterns is provided. The method comprises: receiving a first diffraction pattern; receiving a second diffraction pattern; receiving a third diffraction pattern; determining a first similarity between the first and the second diffraction patterns; determining a second similarity between the first and the third diffraction patterns; determining a third similarity between the second and the third diffraction patterns; and performing hierarchical cluster analysis on the first, the second, and the third diffraction pattern based on the determined first similarity, the second similarity, and the third similarity.

Further consistent with the present invention, a system for analyzing patterns is provided. The system comprises: a memory; and a processor coupled to the memory. The processor is for: receiving a first diffraction pattern; receiving a second diffraction pattern; receiving a third diffraction pattern; determining a first similarity between the first and the second diffraction patterns; determining a second similarity between the first and the third diffraction patterns; determining a third similarity between the second and the third diffraction patterns; and performing hierarchical cluster analysis on the first, the second, and the third diffraction pattern based on the determined first similarity, the second similarity, and the third similarity.

Further consistent with the present invention, a machine-readable magnetic medium comprising instructions stored on the medium is provided. The instruction when executed perform the stages of: receiving a first diffraction pattern; receiving a second diffraction pattern; receiving a third diffraction pattern; determining a first similarity between the first and the second diffraction patterns; determining a second similarity between the first and the third diffraction patterns; determining a third similarity between the second and the third diffraction patterns; and performing hierarchical cluster analysis on the first, the second, and the third diffraction pattern based on the determined first similarity, the second similarity, and the third similarity.

Consistent with the present invention, a method of analyzing patterns is provided. The method comprises: receiving a first diffraction pattern; receiving a second diffraction pattern; receiving a third diffraction pattern; determining a first similarity between the first and the second diffraction patterns based on the characteristic peaks of the first and the second diffraction patterns; determining a second similarity between the first and the third diffraction patterns based on the characteristic peaks of the first and the third diffraction patterns; determining a third similarity between the second and the third diffraction patterns based on the characteristic peaks of the second and the third diffraction patterns; and performing hierarchical cluster analysis on the first, the second, and the third diffraction pattern based on the determined first, the second, and the third similarity.

Further consistent with the present invention, a system for analyzing patterns is provided. The system comprises: a memory; and a processor coupled to the memory. The processor is for: receiving a first diffraction pattern; receiving a second diffraction pattern; receiving a third diffraction pattern; determining a first similarity between the first and the second diffraction patterns based on the characteristic peaks of the first and the second diffraction patterns; determining a second similarity between the first and the third diffraction patterns based on the characteristic peaks of the first and the third diffraction patterns; determining a third similarity between the second and the third diffraction patterns based on the characteristic peaks of the second and the third diffraction patterns; and performing hierarchical cluster analysis on the first, the second, and the third diffraction pattern based on the determined first, the second, and the third similarity.

Further consistent with the present invention, a machine-readable magnetic medium comprising instructions stored on the medium is provided. The instruction when executed perform the stages of: receiving a first diffraction pattern; receiving a second diffraction pattern; receiving a third diffraction pattern; determining a first similarity between the first and the second diffraction patterns based on the characteristic peaks of the first and the second diffraction patterns; determining a second similarity between the first and the third diffraction patterns based on the characteristic peaks of the first and the third diffraction patterns; determining a third similarity between the second and the third diffraction patterns based on the characteristic peaks of the second and the third diffraction patterns; and performing hierarchical cluster analysis on the first, the second, and the third diffraction pattern based on the determined first, the second, and the third similarity.

Consistent with the present invention, a method of analyzing patterns is provided. The method comprises: receiving a first diffraction pattern; receiving a second diffraction pattern; receiving a third diffraction pattern; determining a first similarity between the first and the second diffraction patterns based on the intensity envelopes of the first and the second diffraction patterns; determining a second similarity between the first and the third diffraction patterns based on the intensity envelopes of the first and the third diffraction patterns; determining a third similarity between the second and the third diffraction patterns based on the intensity envelopes of the second and the third diffraction patterns; and performing hierarchical cluster analysis on the first, the second, and the third diffraction pattern based on the determined first, the second, and the third similarity.

Further consistent with the present invention, a system for analyzing patterns is provided. The system comprises: a memory; and a processor coupled to the memory. The processor is for: receiving a first diffraction pattern; receiving a second diffraction pattern; receiving a third diffraction pattern; determining a first similarity between the first and the second diffraction patterns based on the intensity envelopes of the first and the second diffraction patterns; determining a second similarity between the first and the third diffraction patterns based on the intensity envelopes of the first and the third diffraction patterns; determining a third similarity between the second and the third diffraction patterns based on the intensity envelopes of the second and the third diffraction patterns; and performing hierarchical cluster analysis on the first, the second, and the third diffraction pattern based on the determined first, the second, and the third similarity.

Further consistent with the present invention, a machine-readable magnetic medium comprising instructions stored on the medium is provided. The instruction when executed perform the stages of: receiving a first diffraction pattern; receiving a second diffraction pattern; receiving a third diffraction pattern; determining a first similarity between the first and the second diffraction patterns based on the intensity envelopes of the first and the second diffraction patterns; determining a second similarity between the first and the third diffraction patterns based on the intensity envelopes of the first and the third diffraction patterns; determining a third similarity between the second and the third diffraction patterns based on the intensity envelopes of the second and the third diffraction patterns; and performing hierarchical cluster analysis on the first, the second, and the third diffraction pattern based on the determined first, the second, and the third similarity.

Further consistent with the present invention, a method of analyzing a pattern of a disordered form is provided. The method comprises receiving a diffraction pattern of the disordered form; simulating a simulated disordered form based on the peak list of the ordered form; and matching the simulated disordered form to the diffraction pattern of the disordered form.

Further consistent with the present invention, a system for analyzing a pattern of a disordered form is provided. The system comprises memory coupled to a processor, the processor for: receiving a diffraction pattern of the disordered form; simulating a simulated disordered form based on the peak list of the ordered form; and matching the simulated disordered form to the diffraction pattern of the disordered form.

Further consistent with the present invention, a machine-readable magnetic medium comprising instructions stored on the medium is provided. The instruction when executed perform the stages of: receiving a diffraction pattern of the disordered form; simulating a simulated disordered form based on the peak list of the ordered form; and matching the simulated disordered form to the diffraction pattern of the disordered form.

Further consistent with the present invention, a method is described for matching patterns. The method comprises: performing pattern matching on three or more patterns to determine similarities between the patterns; and performing hierarchical cluster analysis on the three or more patterns based on the determined similarities.

BRIEF DESCRIPTION OF THE DRAWINGS

The accompanying drawings, which are incorporated in and constitute a part of this specification, illustrate a system consistent with the invention and, together with the description, serve to explain the principles of the invention.

DETAILED DESCRIPTION

Figure 1:
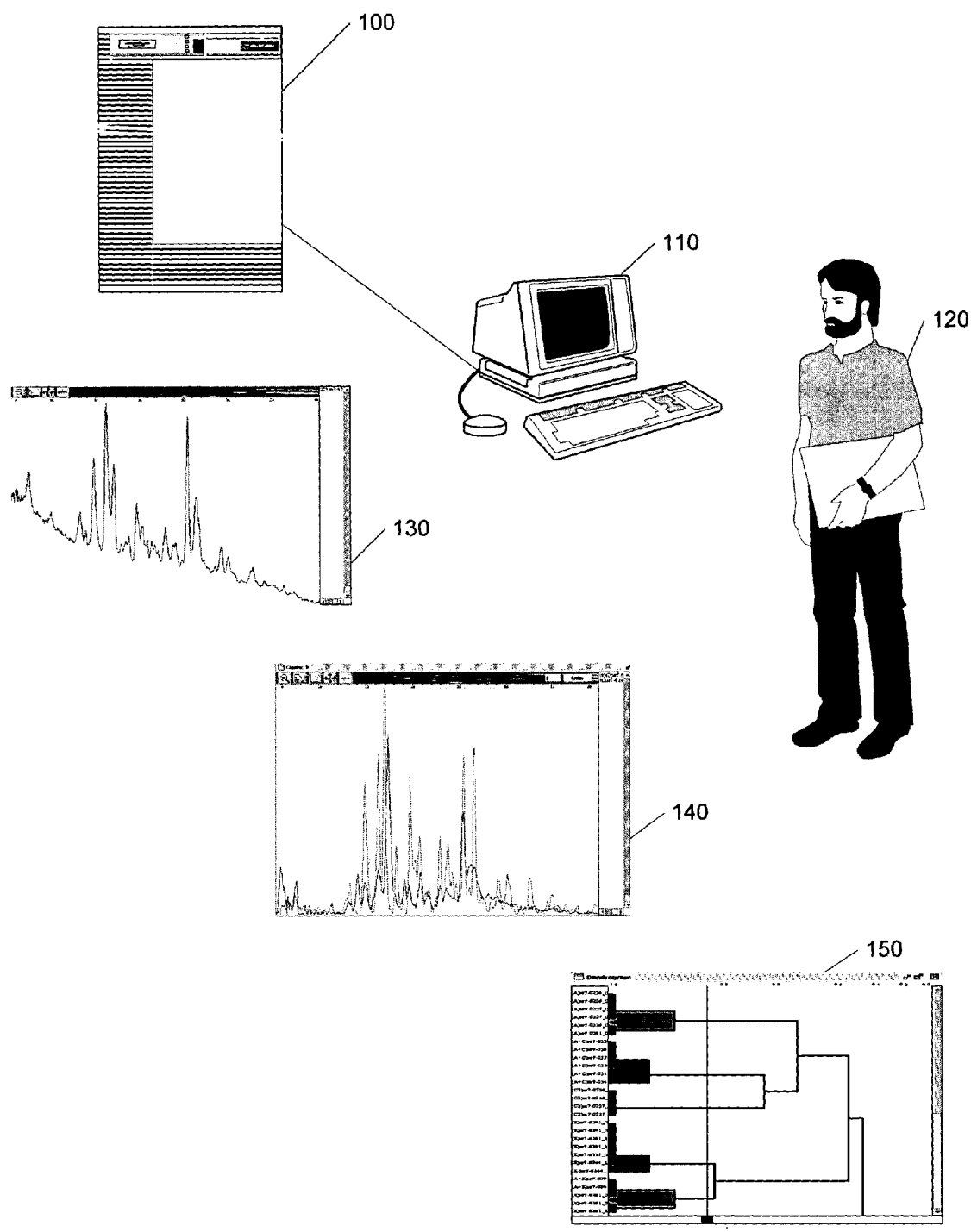
FIG. 1 is an illustration of a system consistent with the present invention in its operating environment.

Reference will now be made in detail to the present exemplary embodiments consistent with the invention, examples of which are illustrated in the accompanying drawings. Wherever possible, the same reference numbers will be used throughout the drawings to refer to the same or like parts.

The clustering of measured diffraction patterns from polycharacteristic materials, noncrystalline materials, or mixtures is an example of clustering objects where the measure of similarity is not obvious and is an area where HCA has not previously been applied. Many experimental variables (sample preparation, instrumental variation, random noise) make the selection of a robust measure of similarity for diffraction patterns a complex procedure.

Based upon many years of experience in manually clustering 'similar' diffraction patterns, a set of Heuristic laws has been derived that allows direct quantification of the similarity between two or more measured diffraction patterns. This measure of similarity may then be used with an HCA procedure to identify groups of relatively similar diffraction patterns.

At least two distinct measures of similarity may be implemented for the purpose of clustering diffraction patterns. The first may determine the similarity of diffraction patterns according to the 'similarity' of the measured diffraction peaks, while the second may determine the similarity of diffraction patterns according to the 'similarity' of the measured intensity envelope.

Diffraction patterns from crystalline material with 'similar' crystallographic unit cell parameters may generate diffraction patterns with 'similar' measured diffraction peak positions. The more similar the crystallographic unit cell parameters the more similar the measured diffraction peak positions.

Crystalline material with 'similar' molecular or atomic packing motifs may generate diffraction patterns with 'similar' measured intensity envelopes within the limits imposed by sample preparation variables. The more similar the molecular or atomic packing motifs, the more similar the measured intensity envelopes.

Clustering measured crystalline diffraction patterns based upon the similarity of the measured peak positions and intensities allow, therefore, the grouping of samples containing predominantly the same crystalline polymorph. That is, the same crystallographic unit-cell, the same point group and space group, and the same molecular/atomic-packing motif. Samples containing predominantly the same polymorph are most likely to exhibit similar chemical behavior.

Using only the measured intensity envelope as a measure of similarity between diffraction patterns allows for the grouping of samples that are iso-structural. Having similar molecular/atomic-packing motif but differing unit cell parameters characterize iso-structural materials. The difference between one iso-structural material and another is a difference in unit cell parameters (a symmetry translation) that will not affect the chemical properties. Like samples containing the same polymorphs, samples that are iso-structural will exhibit similar chemical properties.

Consistent with the principles of the present invention, systems may be utilized, for example, to identify new solid forms of compounds or elements. They may be used, for example, to identify new solid forms of known drugs. These new solid forms of drugs may provide improved properties, such as improved stability, solubility, bioavaliability, or handling properties. In order to find a new solid form of a drug, the drug may be crystallized in many different ways. For example, hundreds or thousands of samples of the drug may be generated by crystallization or solidification using different solvents, different temperatures, different humidities, or different pressures. Those skilled in the art will appreciate the variety of approaches that may be taken to generate a wide variety of solid forms of a material.

Samples of a material may be, for example, in a crystalline, disordered crystalline, polycrystalline, non-crystalline, amorphous, disordered, microcrystalline, nanocrystalline, partially amorphous, partially crystalline, semisolid, crystal mesophases, or glassy form or mixtures of these forms. Once the samples have been generated, diffraction instrumentation may be utilized to analyze the samples and produce diffraction patterns. Diffraction patterns may be, for example, neutron diffraction patterns, X-ray diffraction patterns, or electron diffraction patterns. Consistent with the present invention, diffraction patterns of the samples are compared. The results of the comparison of the patterns may be analyzed using hierarchical cluster analysis (HCA) to group the patterns into similar clusters. Further information on hierarchical cluster analysis may be found in C. Olson, "Parallel Algorithms For Hierarchical Clustering," *Parallel Computing*, 21:1313-1325, 1995. Consistent with the principles of the present invention, X-ray diffraction (XRD) and HCA may be combined to find new solid forms of materials, including but not limited to new solid forms of drugs.

FIG. 1 is an illustration of a system consistent with the present invention in its operating environment. Diffraction instrumentation 100 analyzes samples yielding a pattern 130. Pattern 130 is a graph with degrees along the X-axis and magnitude along the Y-axis. Instrumentation 100 may include any type of instrumentation by, for example, manufacturers such as Shimadzu, Bruker, or INEL in the case of X-ray powder diffraction. Pattern 130 is transferred as pattern data to Analysis System 110. The transfer may be by transfer of storage media, such as floppy disk, hard disk, tape, or flash ram, or by electronic means, such as over a Local Area Network, Wide Area Network, the Internet, or point-to-point communication via a modem, Firewire, USB, serial, or parallel connection.

Analysis System 110 may be operated by an Operator 120 or may function without the intervention of an operator. Analysis System 110 may perform matching on the patterns in order to quantify the similarity between at least a first pattern and a second pattern. Consistent with the present invention, each pattern may be compared to every other pattern received to generate a quantitative similarity between each pattern and every other pattern. Patterns that are identical may be ignored and patterns composed of mixtures of other patterns may be determined.

Analysis System 110 may match patterns by several methods, including: identifying peaks within the patterns and matching the patterns based on the identified peaks; or matching the intensity envelopes of the patterns. Graph 140 illustrates matching two patterns based on identified peaks. Analysis System 110 may quantify the similarities between the patterns. The pattern matching scores or similarity scores may be used to perform HCA analysis on the patterns to yield a Dendrogram 150. Dendrogram 150 illustrates the grouping of patterns into clusters of similar forms. This cluster analysis will group similar patterns together for further use.

Figure 2:
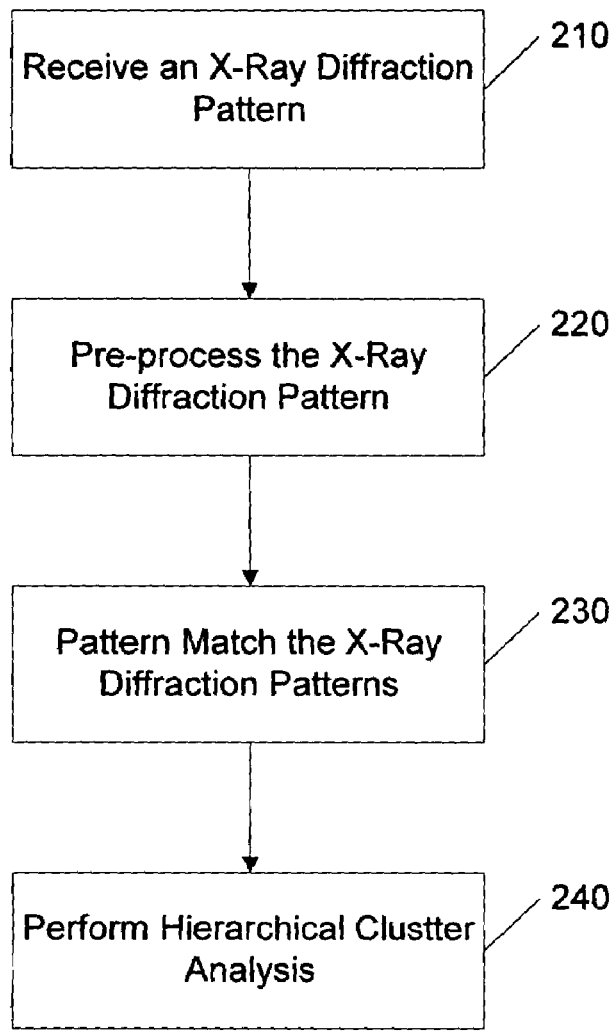
FIG. 2 is a flowchart of the operation of the Analysis System consistent with the present invention.

FIG. 2 is a flowchart of the operation of the Analysis System 110 consistent with the present invention. Analysis System 110 may perform the similarity determination and HCA analysis method 200 through one or more of the following methods: receives the patterns, pre-processes the patterns, matches the patterns to generate a similarity score between the patterns, and performs hierarchical cluster analysis on the patterns based on the similarity scores. At stage 210, the method 200 receives two or more patterns. These patterns may be in the form of a graphical image converted to a flat data file through image scanning and analysis or may arrive in a flat data file, such as an ASCII comma or tab delimited format, SQL data, or spreadsheet data.

At stage 220, each pattern may be pre-processed. The pre-processing stage 220 may vary depending on the pattern matching technique utilized later in method 200. The pre-processing stage 220, generally, may massage the data to normalize the data, remove instrumentation errors and variations, and analyze the data for results used later in method 200.

At stage 230, method 200 may match the patterns to each other to determine their similarities. Stage 230 may match peaks within the patterns to determine similarity or may match the general intensity envelopes of the patterns to determine similarity. Peak matching is useful for identifying similar unit cells and crystal symmetry. Intensity envelope matching is useful for identifying isostructures of the crystalline forms and clustering disordered forms with ordered forms.

Figure 23A:
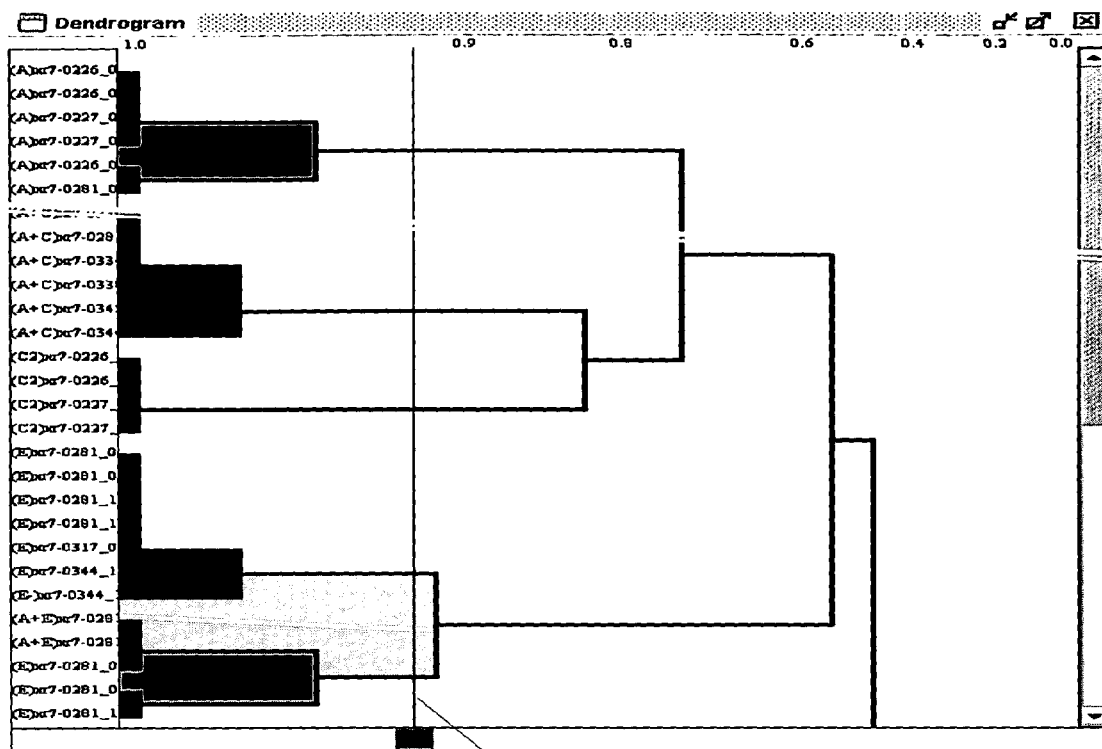
FIGS. 23a and 23b illustrate the results of a hierarchical cluster analysis generated by methods consistent with the present invention.
Figure 23B:
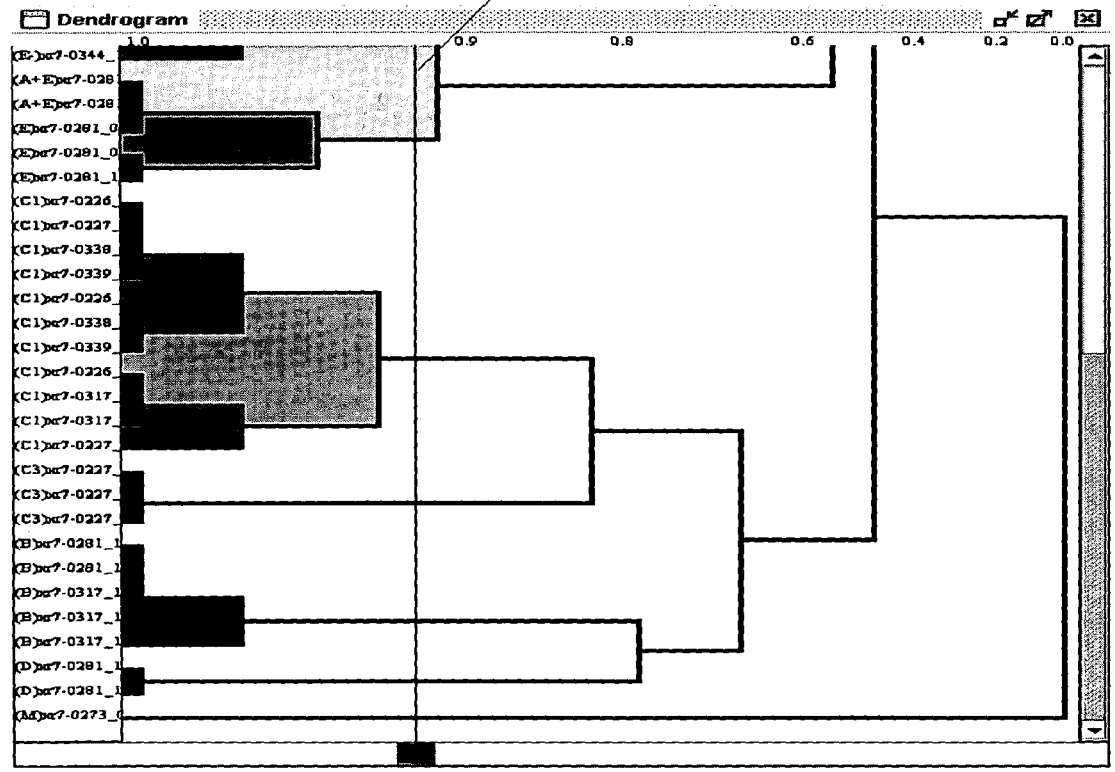

At stage 240, the results of the matching, i.e. the similarity scores, are utilized to perform hierarchical cluster analysis (HCA), described in more detail in the following paragraphs. Initially, HCA defines every pattern as a separate cluster. The two most similar clusters are aggregated into a cluster. The clustering then repeats until all clusters are joined together. The resulting clustering is displayed in a tree structure, known as a dendrogram. FIGS. 23*a* and 23*b*, to be discussed later, illustrate an exemplary dendrogram. The vertical axis displays each sample. Patterns that are similar cluster together toward the left portion of the horizontal axis. As similarity diverges, the clusters are grouped together toward the right portion of the horizontal axis. Thus, moving from left to right, the horizontal axis displays lesser degrees of similarity. Similarity is relatively scaled so that a similarity of 1.0 denotes a perfect match with perfect similarity and a similarity of 0.0 denotes the poorest match.

While those skilled in the art will understand HCA, a short description of a basic HCA method follows: Starting with a set of N items (consistent with the present invention, N patterns), and an N×N similarity matrix describing the relative similarity of each item to each other item, the basic process of HCA is:

1. Initially assign each item to its own cluster, producing N clusters, each containing one item. Let the similarities between the clusters equal the similarities between the items they contain.

2. Find the most similar pair of clusters and merge them into a single cluster, resulting in one less cluster (for an initial total of N−1 clusters).

3. Compute similarities between the new cluster and each of the remaining old clusters.

4. Repeat steps 2 and 3 until all items are clustered into a single cluster of size N. Each merge operation can be considered as a branch in a tree of clusters. As previously explained, this tree is called a dendrogram and has its root in the final cluster that contains all N items. The leaves of the tree are the initial N single item clusters.

Step 3 may be done in different ways, resulting in different cluster distance metrics. Some of the most commonly used cluster distance metrics are: single-link, complete-link and average-link. In single-link clustering (also called the minimum method), the similarity between two clusters is equal to the greatest similarity from any item in one cluster to any item in the other cluster. In complete-link clustering (also called the maximum method), the similarity between two clusters is equal to the smallest similarity from any item in one cluster to any item in the other cluster. In average-link clustering, the similarity between two clusters is equal to the average similarity from any item in one cluster to any item in the other cluster. HCA may be understood in more detail in the following references, each of which is incorporated by reference: Borgatti, S. P., "How to Explain Hierarchical Clustering", *Connections*, 17(2):78-80, 1994; Johnson, S. C., "Hierarchical Clustering Schemes" *Psychometrika*, 2:241-254, 1967; Olson, C., "Parallel Algorithms For Hierarchical Clustering", *Parallel Computing*, 21:1313-1325, 1995.

HCA stage 240 may provide an interface that allows the user to intersect a number of branches of the tree, where each intersected branch corresponds to a cluster (form) containing patterns with similarity greater than the intersection number. The user interface may be in the form of a vertical bar 2310. Thus, the form bar segments the dendrogram into a number of clusters, where the number of clusters or forms will vary depending on the horizontal positioning of the form bar. HCA stage 240 may select an optimum position for the form bar, or cutoff similarity, based on the similarities determined in stage 230. The optimum position of the form bar may be selected at a point between 0.0 and 1.0 and may be adjusted up or down based on the similarity of the patterns.

In addition, HCA stage 240 may provide for a post-HCA mixture analysis. In post-HCA mixture analysis, representative peaks for a first cluster may be compared to combinations of two or more clusters searching for combinations of clusters having peaks that match the first cluster. This may be repeated across all clusters, flagging mixtures for the operator. For example, in an HCA analysis yielding 10 clusters, the first cluster may be compared to various combinations of the $2^{nd}$ through $10^{th}$ clusters searching for matching of characteristic peaks of the first cluster with characteristic peaks of the combined clusters. This may continue for each of the $2^{nd}$ through $10^{th}$ clusters.

In addition, stages 230 and 240 may be performed separately based on the type of patterns analyzed. For example, crystalline forms may be only matched against crystalline forms, amorphous or other forms that generate broad features may be only matched against other forms that generate broad features, and mixtures of broad feature and crystalline forms may be only matched against mixtures of broad feature and crystalline forms. Also, the pattern matching algorithm used may vary depending on the type of peak. For example, the peak matching algorithm may be utilized with crystalline forms, and the envelope matching algorithm may be utilized with forms that generate broad features.

Figure 3:
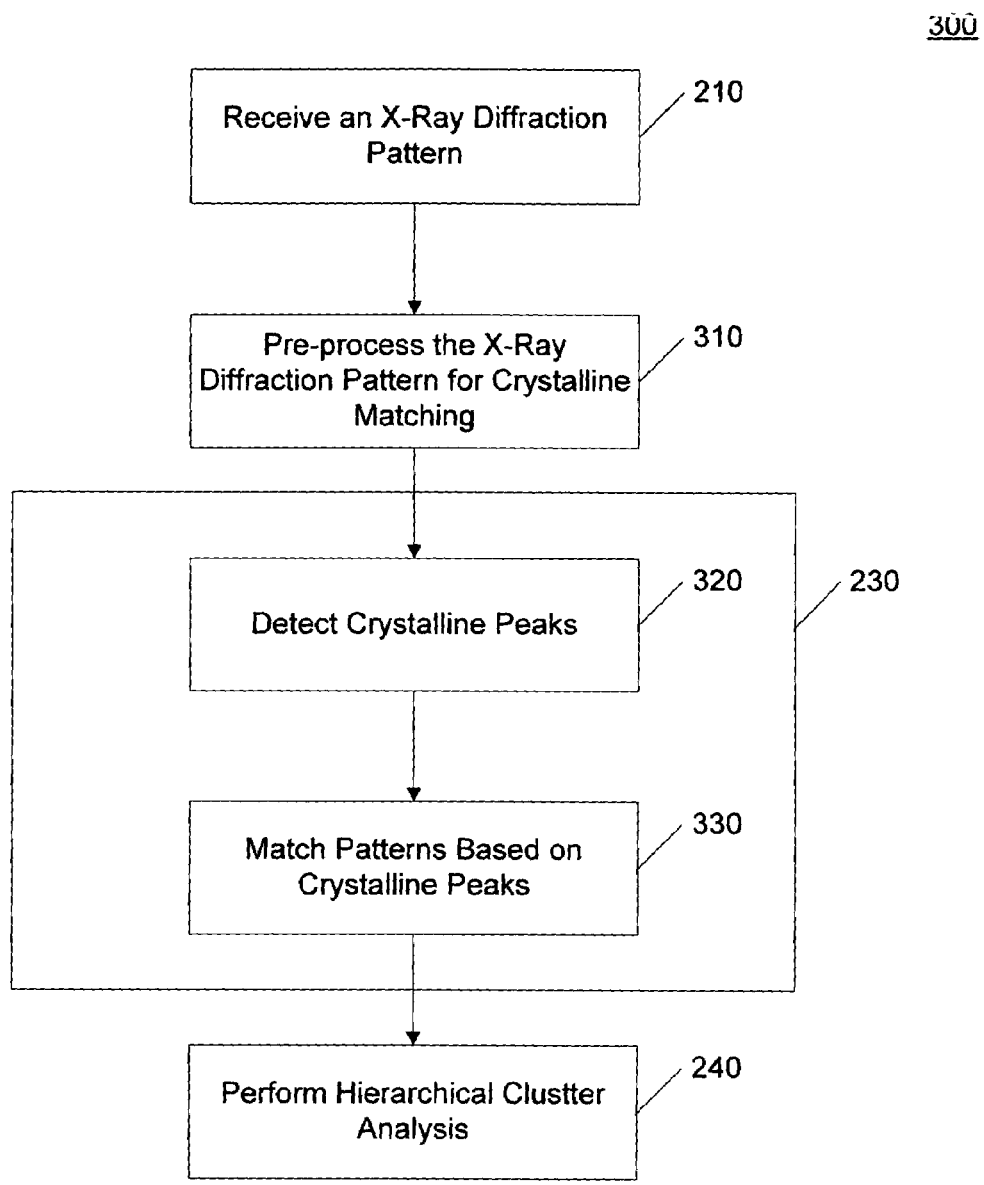
FIG. 3 is a flowchart of the operation of the peak comparison methodology of the Analysis System consistent with the present invention.

FIG. 3 is a flowchart of the operation of the peak comparison methodology of the Analysis System consistent with the present invention. At stage 210, a pattern is received as previously described. At stage 310, the pattern may be pre-processed. Pre-processing the pattern may comprise one or more of: correcting for baseline shift, smoothing the pattern, removing broad features, computing variance, and detecting the potential presence of preferred orientation and particle statistics (any reference to preferred orientation and particle orientation shall presume to be interpreted as both the conjunctive and disjunctive form). Pre-processing stage 310 is further explained with reference to FIG. 4 that follows. At stage 320, the peaks of the pattern may be detected, listed, and categorized. At stage 330, the listed and categorized peaks of the pattern may be compared to the listed and categorized peaks of the other sample patterns. The result of stage 330 may be a measure of the similarity between the pattern and other patterns. Finally, as previously described, the similarity measure of the patterns is used to perform HCA analysis at stage 240.

Figure 4:
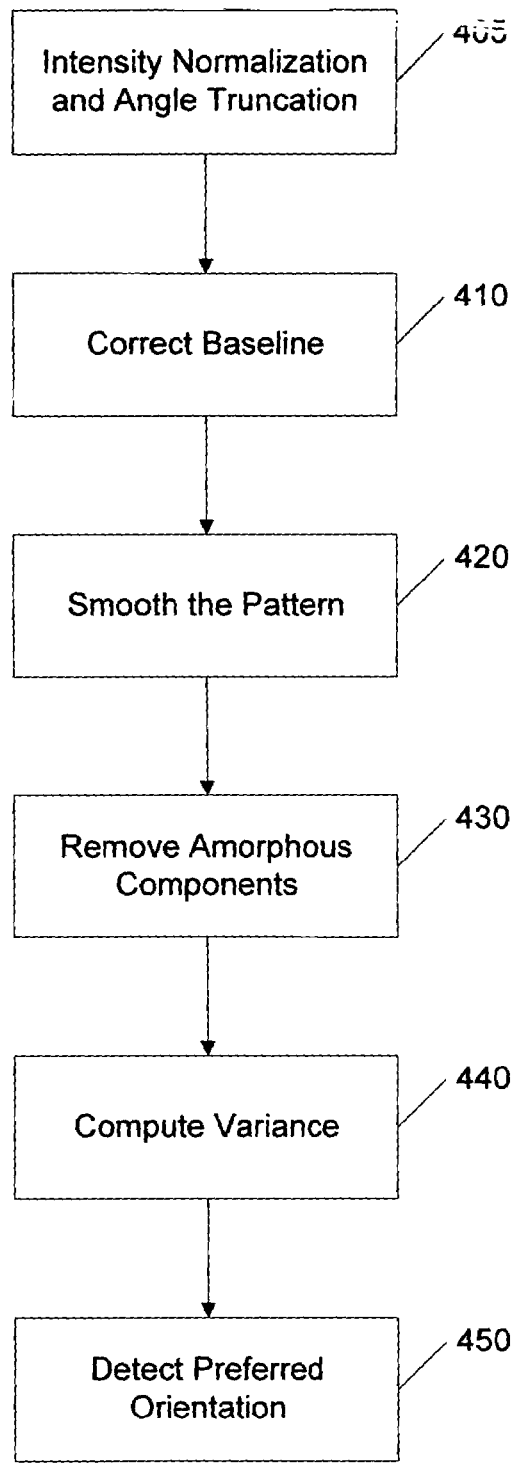
FIG. 4 is a flowchart of the peak comparison pre-processing method consistent with the present invention.
Figure 10:
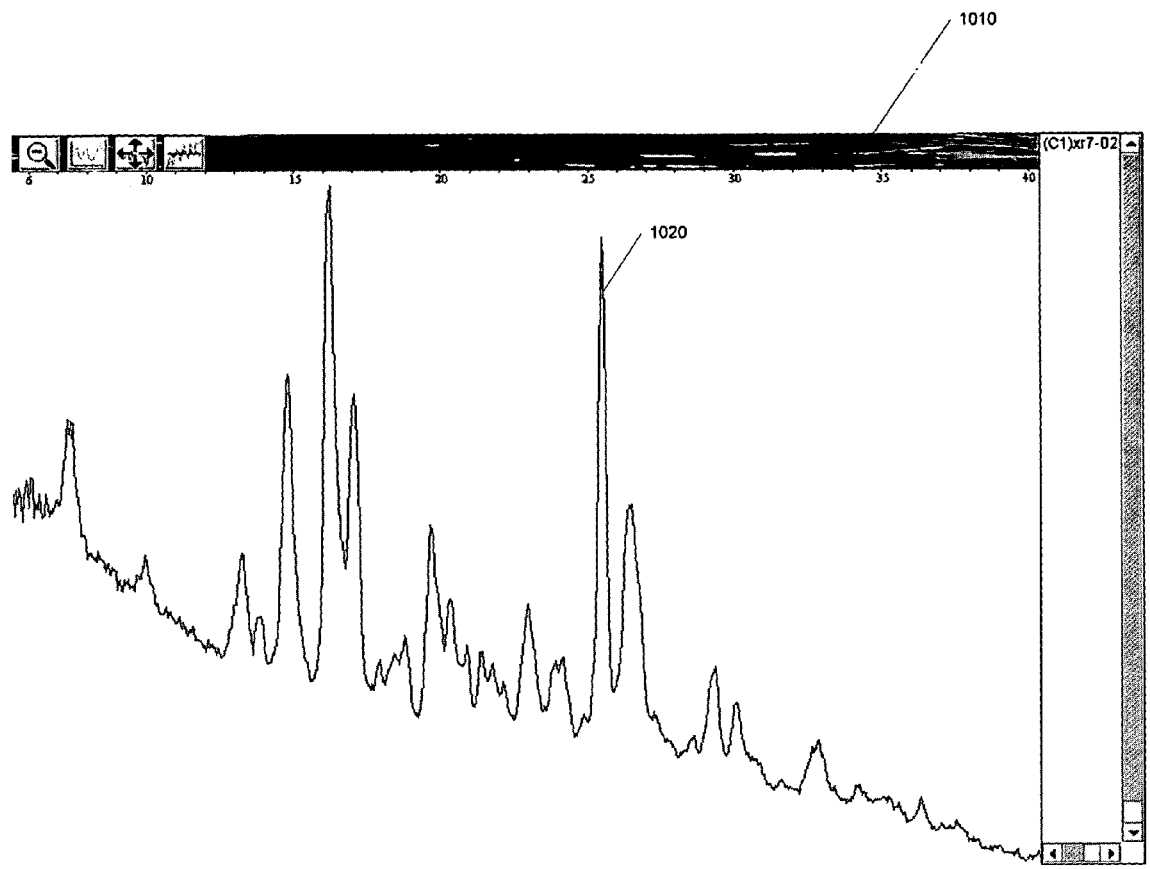
FIG. 10 is an illustration of a diffraction pattern analyzed in the present invention.
Figure 11:
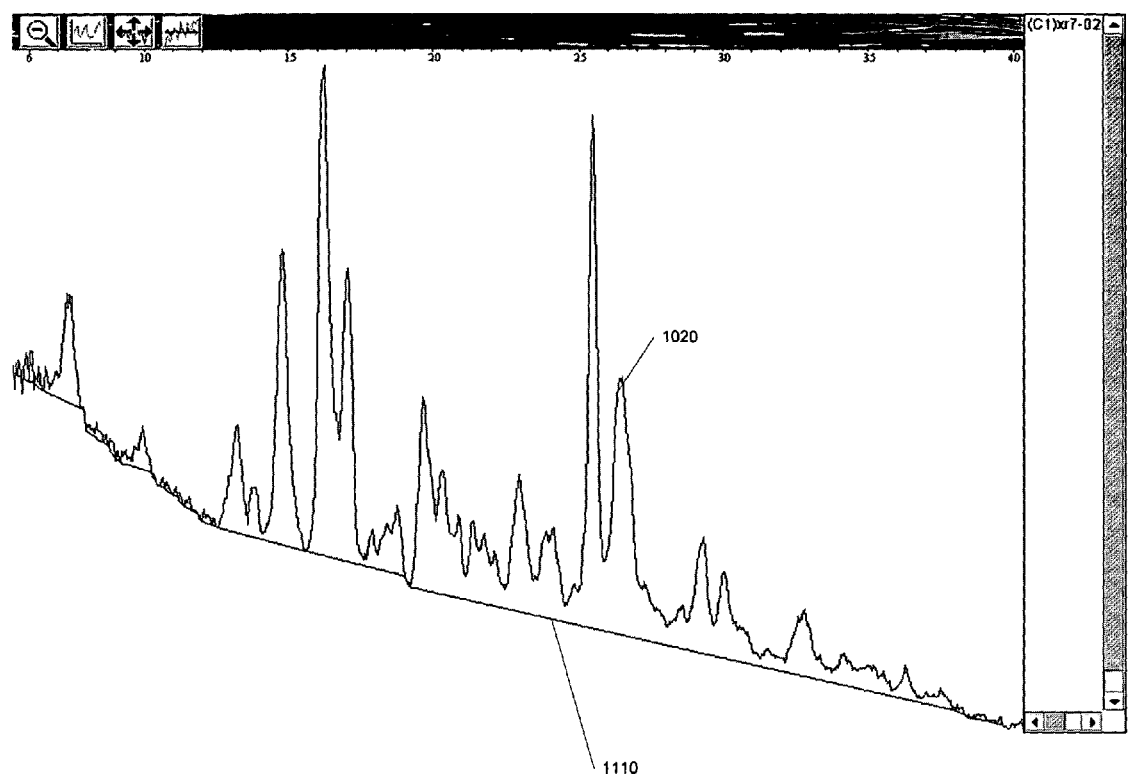
FIG. 11 is an illustration of the diffraction pattern and the diffraction pattern baseline determined by methods consistent with the present invention.
Figure 12:
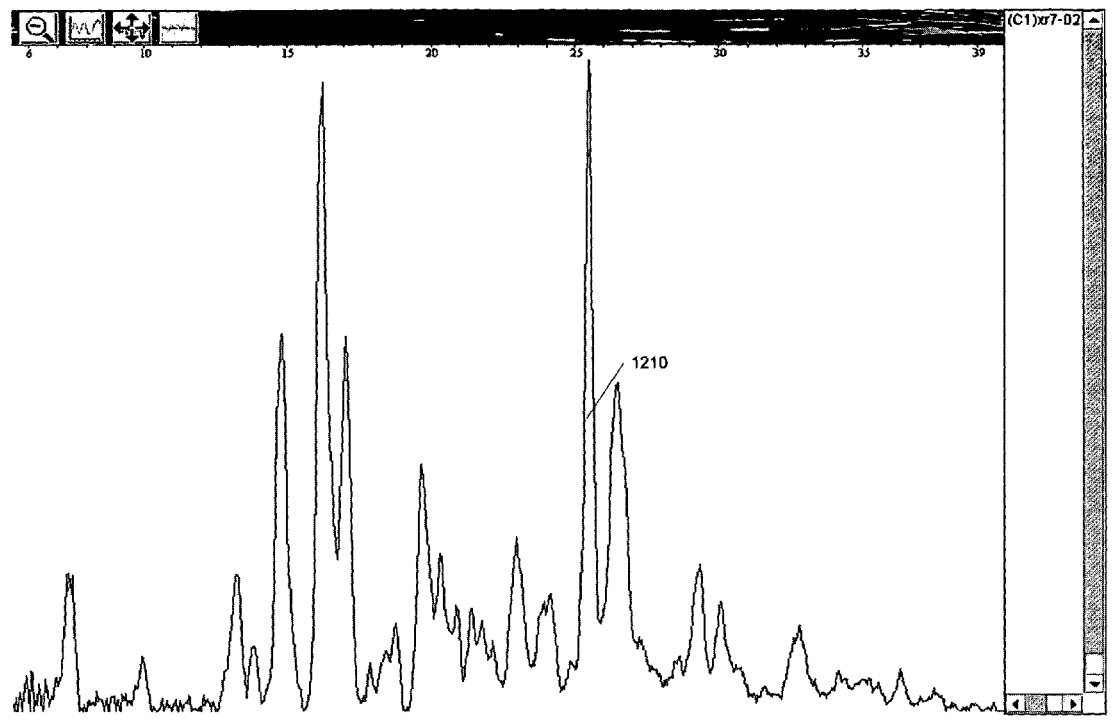
FIG. 12 is an illustration of the baseline corrected diffraction pattern determined by methods consistent with the present invention.

FIG. 4 is a flowchart of the peak comparison pre-processing method 310 consistent with the present invention. At stage 405, the pattern intensities may be normalized to a scale of [0,1] to avoid common potential presence of preferred orientation and particle statistics effects. In addition, the pattern may be truncated to a standard x range used in the pattern matching, for example 2.5° to 40°. Data outside of the truncated range may be discarded. At stage 410, the baseline of the normalized, truncated, pattern is detected and the pattern may be baseline corrected. FIG. 10 illustrates a raw input pattern 1020. Notice that there is a general shift in the pattern from the upper left to the lower right. This is a baseline shift. FIG. 11 illustrates the detected baseline 1110 of pattern 1020. Stage 410 may examine the local minima across a sliding window of pattern 1020 to determine baseline 1110 or employ a digital filter algorithm for a similar purpose. Following baseline correction, a baseline corrected pattern 1210, illustrated in FIG. 12, results.

Figure 13:
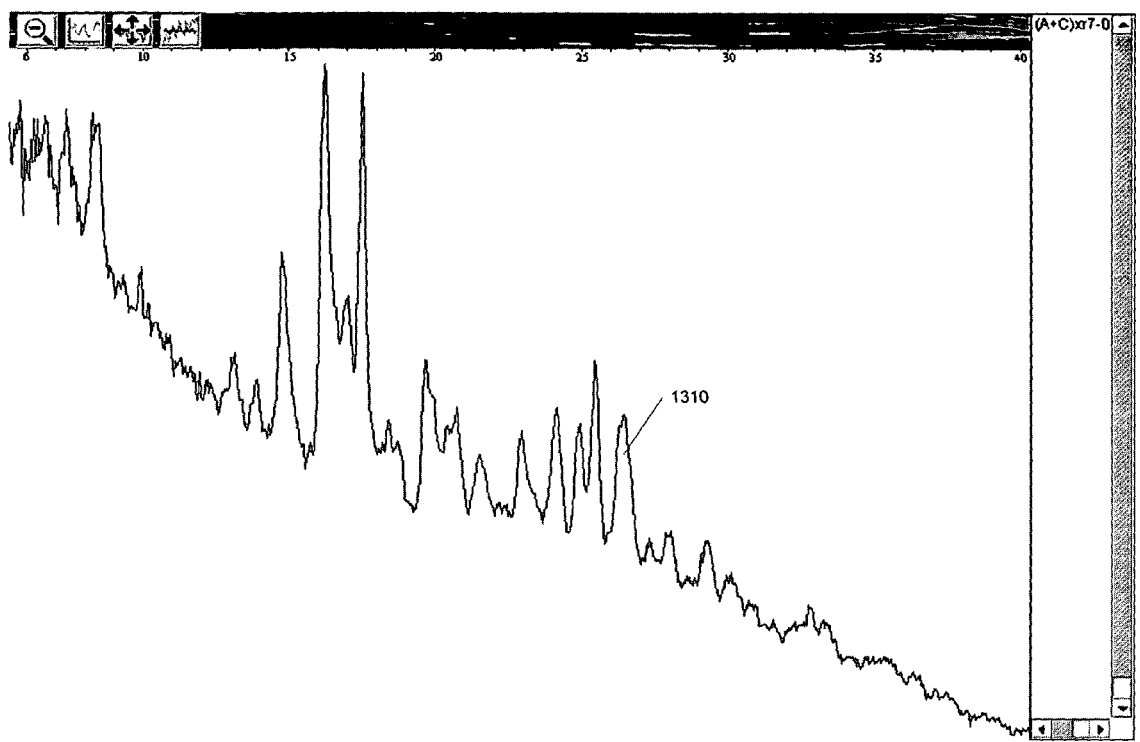
FIG. 13 is an illustration of the diffraction pattern analyzed by methods consistent with the present invention.
Figure 14:
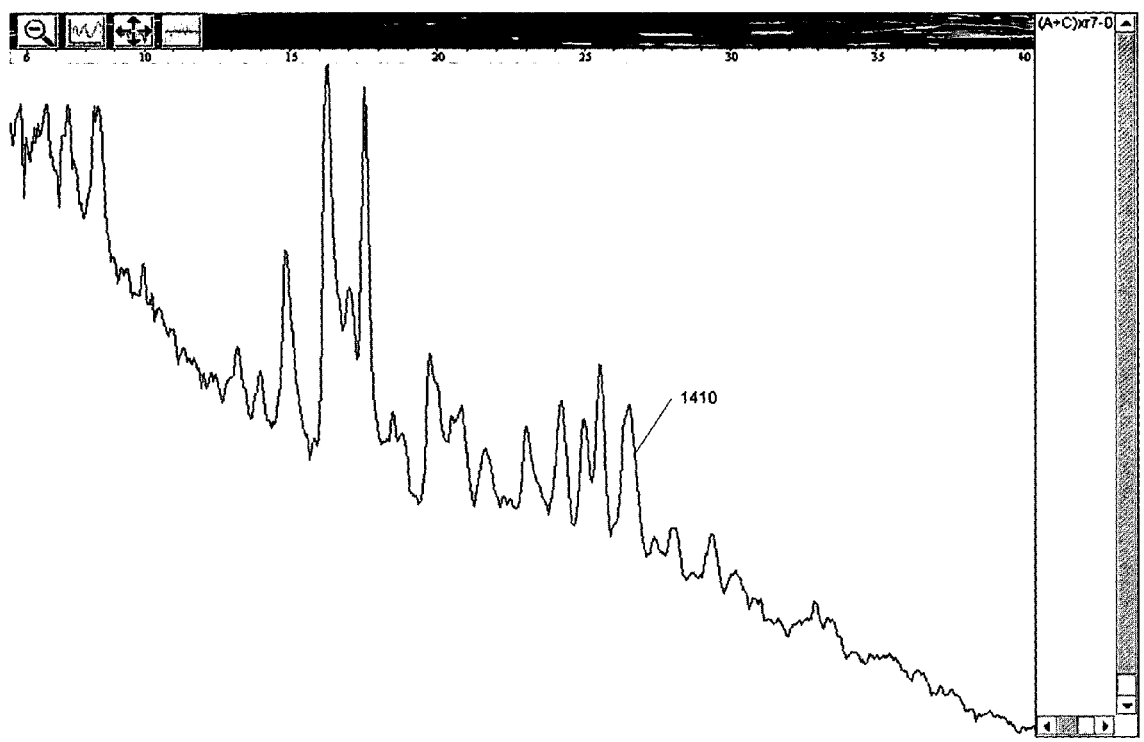
FIG. 14 is an illustration of the smoothed diffraction pattern generated by methods consistent with the present invention.

At stage 420, the pattern is smoothed. Any of a number of smoothing algorithms or filters may be used to smooth the pattern, for example, Savitzky-Golay smoothing or digital filtering. FIG. 13 illustrates a pattern 1310 prior to smoothing. FIG. 14 illustrates a smoothed pattern 1410 based on the pattern 1310.

Figure 15:
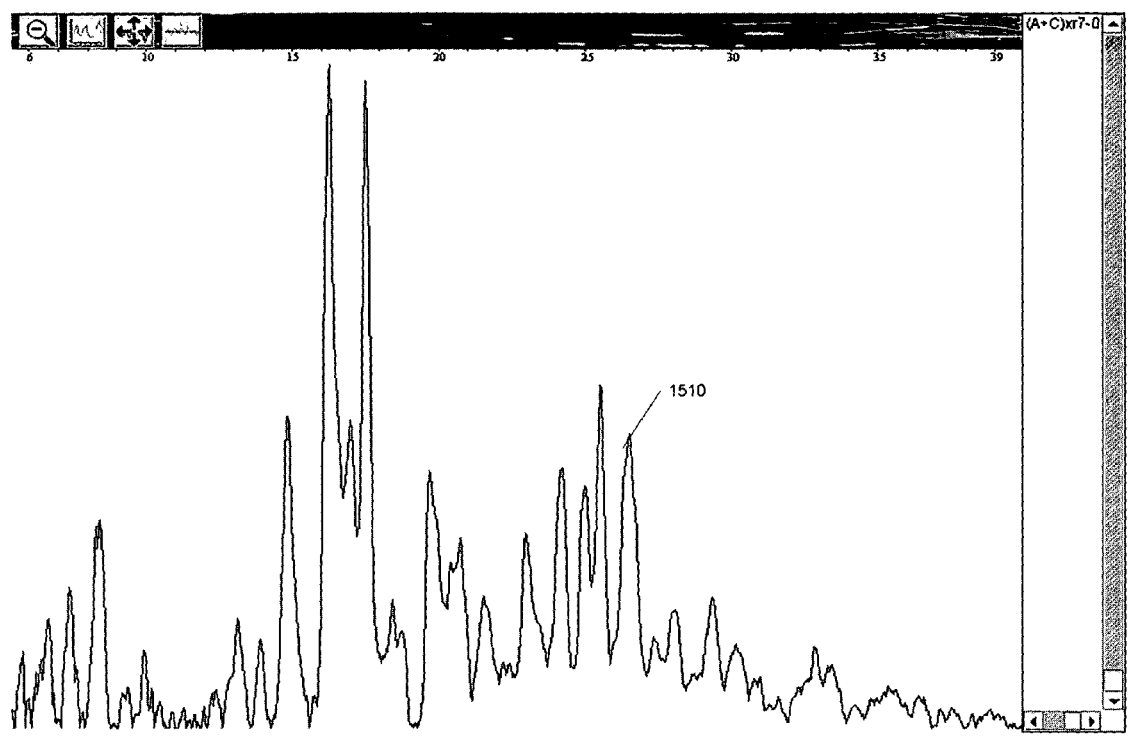
FIG. 15 is an illustration of the smoothed, baseline corrected diffraction pattern generated by methods consistent with the present invention.

Smoothing and baseline correction may be used together during pre-processing to yield a smoothed, baseline corrected pattern, such as pattern 1510 in FIG. 15.

Figure 17:
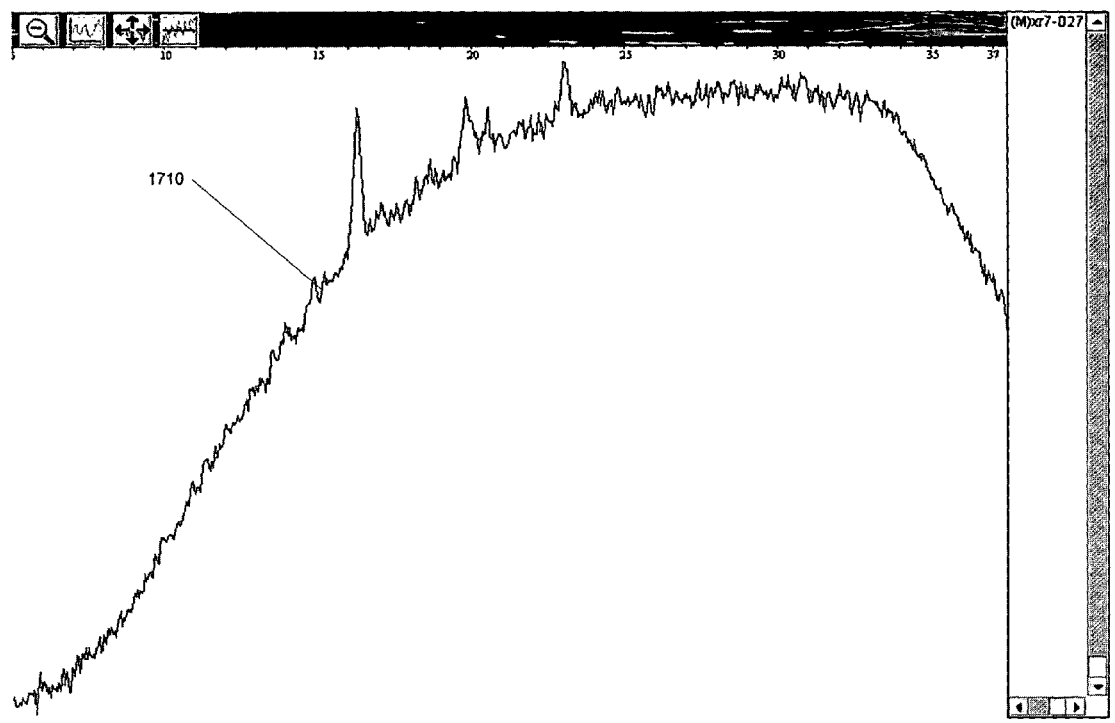
FIG. 17 is an illustration of the diffraction pattern with a broad feature analyzed by methods consistent with the present invention.
Figure 18:
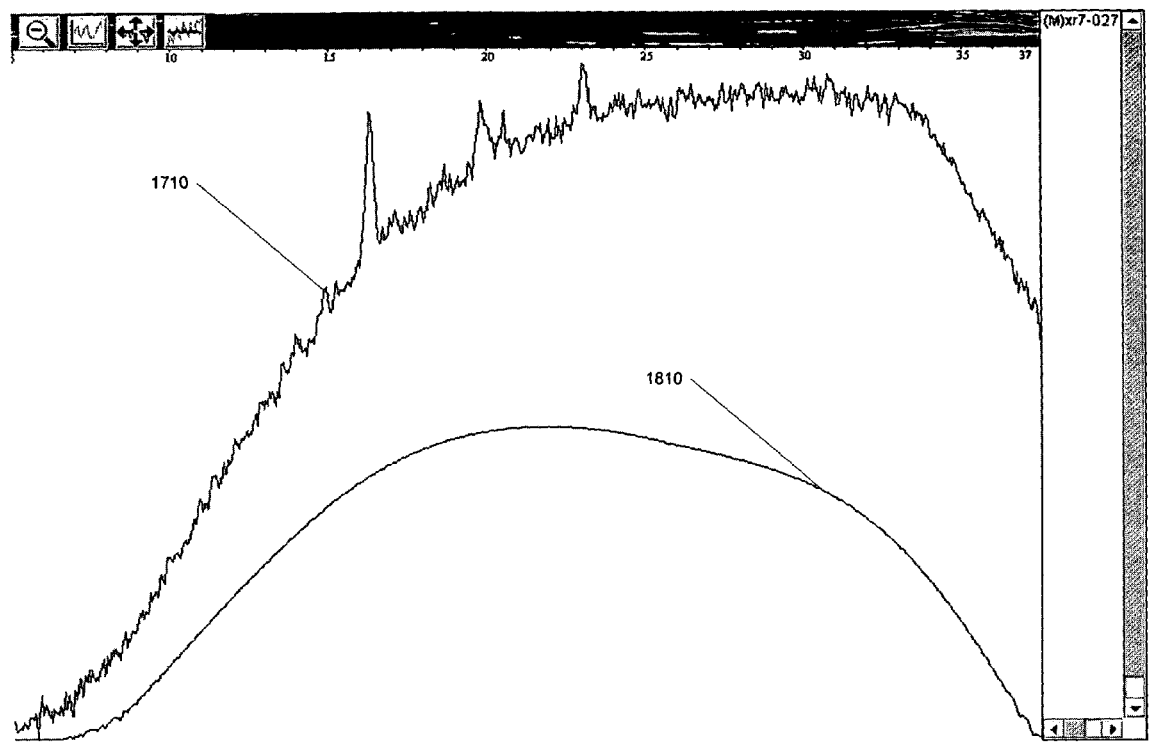
FIG. 18 is an illustration of the diffraction pattern with a broad feature and the broad feature detected by methods consistent with the present invention.
Figure 19:
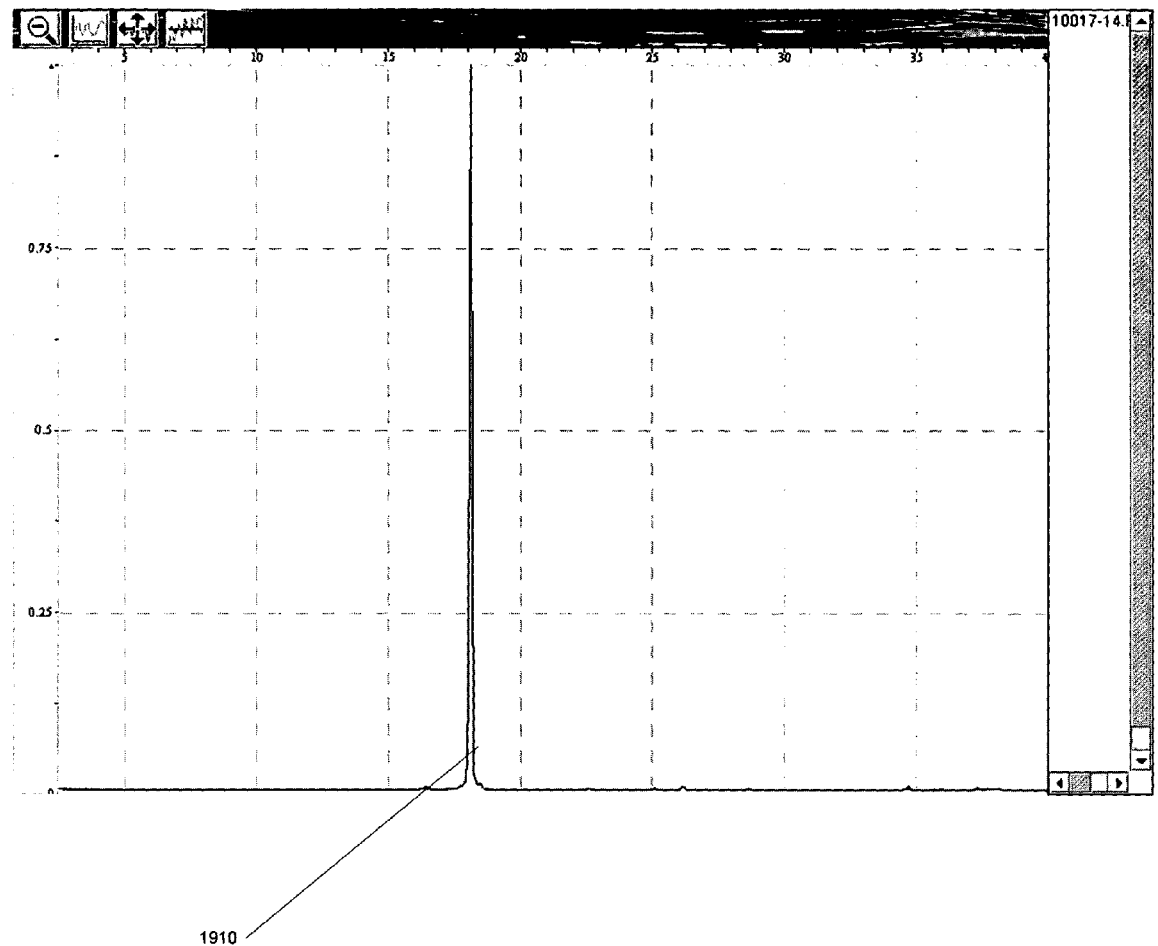
FIG. 19 is an illustration of preferred orientation or particle statistics.

At stage 430, any broad features of the pattern may be detected and removed. Broad features might be produced by amorphous components, disordered crystalline forms, or parasitic scatter form the main beam. Pattern 1710 of FIG. 17 illustrates a pattern with a broad feature. Stage 430 detects the component, illustrated as component 1810, within pattern 1710. Stage 430 may detect the component 1710 by utilizing a heavy and repeated smoothing filter to pattern 1710. Any patterns with broad features detected may be segregated out and matched and clustered separately from patterns that are crystalline and without broad features.

At stage 440, the pre-processing method 310 determines the variance of the pattern. This variance is stored for later use by other portions of the algorithm 300, specifically, for example, for use in peak detection.

At stage 450, the pre-processing method 310 may detect the potential presence of preferred orientation and particle statistics of the sample from the pattern. Preferred orientation and particle statistics is detected if a few peaks are abnormally high when compared to the rest of the peaks. In addition, the noise level of the pattern (possibly represented by the variance) may be considered in making this determination as patterns with potential presence of preferred orientation and particle statistics tend to exhibit low levels of noise after normalization. The potential presence of preferred orientation and particle statistics is flagged and parameters in the rest of the method, for example, the peak detection algorithm, may be adjusted based on this flag. Additionally, the location of these peaks may be stored. For example, pattern 1910 might reveal a potential presence of preferred orientation and particle. In addition, noise may be detected and used to adjust pattern matching parameters.

Figure 5:
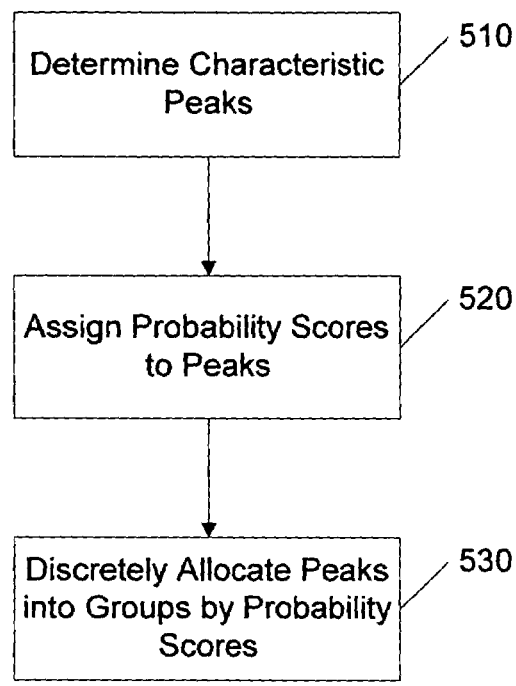
FIG. 5 is a flowchart of the peak detection method consistent with the present invention.

FIG. 5 is a flowchart of the peak detection method 320 consistent with the, present invention. At stage 510, the characteristic peaks are detected. These peaks are points on the pattern that are greater than a minimum height, greater than a minimum width and with a degree of lateral space from their nearest neighbors. Stage 510 is more fully explained later with reference to FIG. 6. At stage 520, probability scores are assigned. Probability scores may be based on the height, width, and neighbors of the characteristic peaks. Stage 520 yields a list of characteristic peaks and scores ranging, for example, between 0 and 100%. Stage 520 is more fully explained with reference to FIG. 7.

Figure 16:
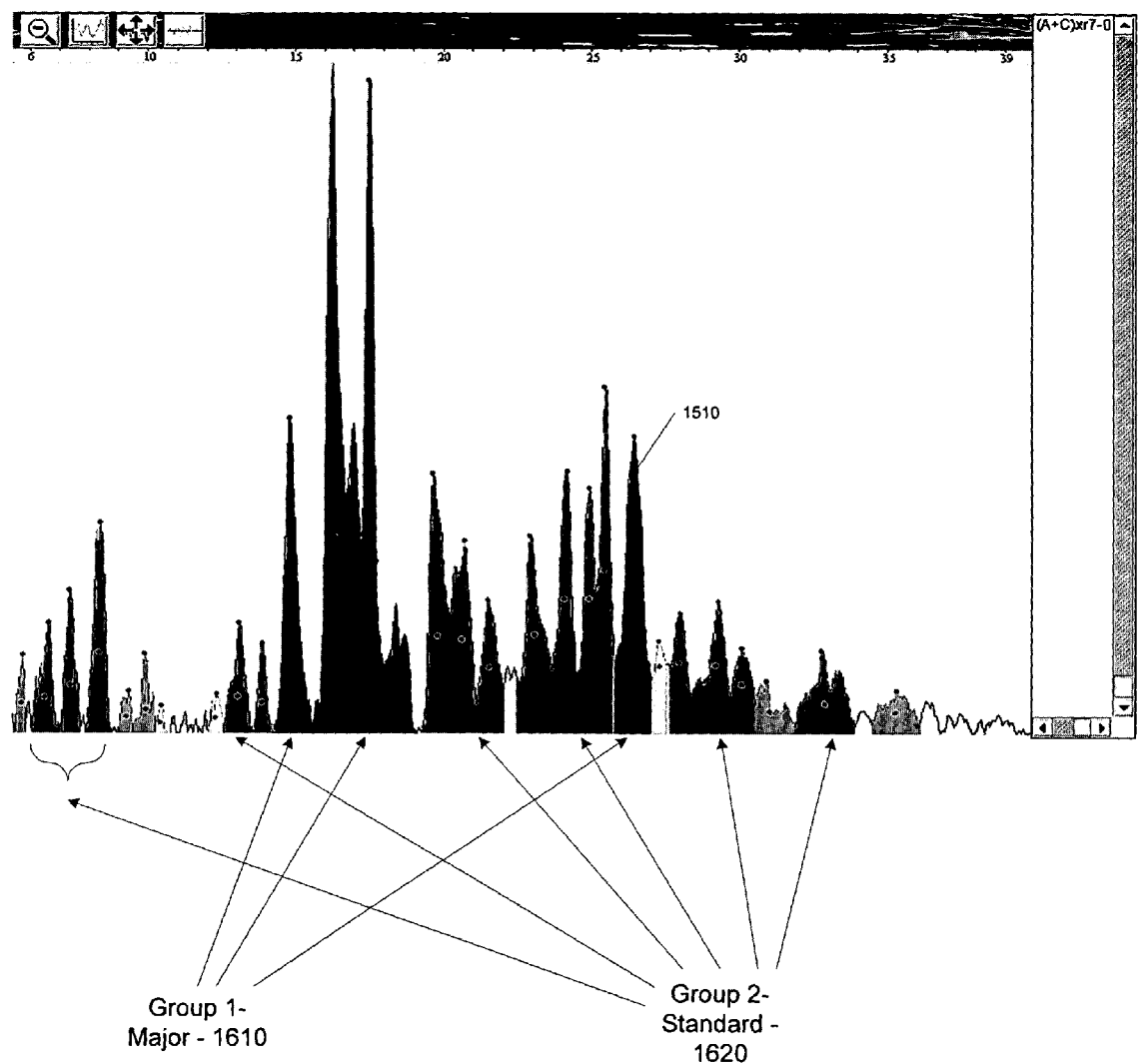
FIG. 16 is an illustration of the smoothed, baseline corrected diffraction pattern with the peaks detected and categorized generated by methods consistent with the present invention.

At stage 530, the characteristic peaks may be allocated into discrete groups based on their associated probability score. For example, major peaks may be grouped into Group 1, lesser peaks into Group 2, and so on through Group 4 (minor peaks). Group 1 may comprise characteristic peaks with scores greater than 75%; group 2 may comprise characteristic peaks with scores greater than 50% to 75%; group 3 may comprise characteristic peaks with scores greater than 25% to 50%; and group 4 may comprise characteristic peaks with scores between 0% and 25%. FIG. 16, discussed later, illustrates characteristic peaks placed into groups. Those skilled in the art would appreciate that fewer or lesser than four groups may be utilized and ranges may vary in discretely allocating the peaks.

Figure 6:
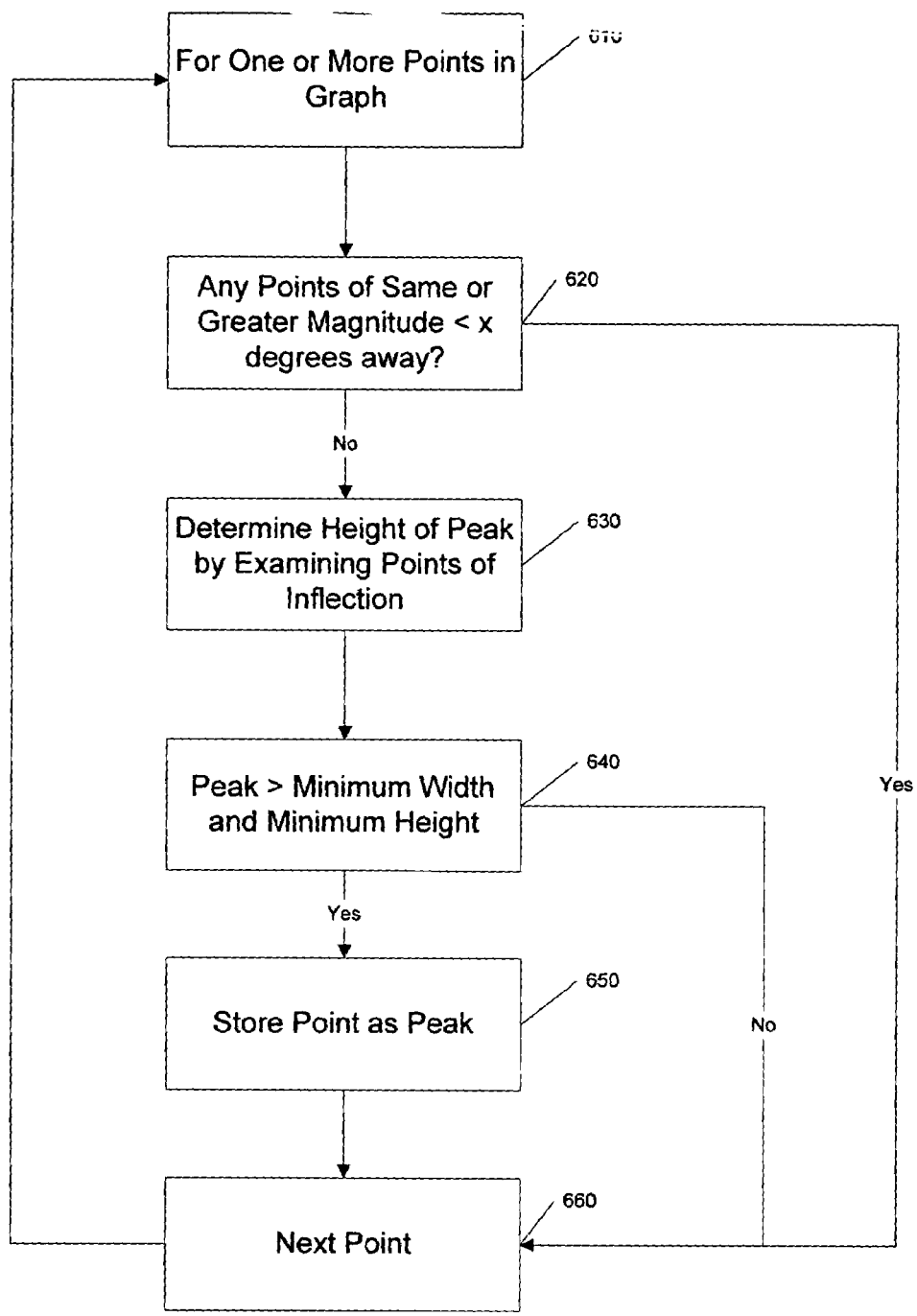
FIG. 6 is a flowchart of the characteristic peak determination method consistent with the present invention.

FIG. 6 is a flowchart of the characteristic peak determination method 510 consistent with the present invention. At stage 610, the process begins at a first point within the pattern. Every single data point may be processed through the methodology of stages. 620-660, or to speed up the process fewer points may be processed, for example every other point may be processed. In general, characteristic peak determination method 510 is looking for peaks of a significant amplitude and width relative to the pattern.

At stage 620, the method looks to see if there are any points of the same or greater magnitude within x degrees of the examined point. If so, processing proceeds to stage 660 and the next point is selected. If not, the point appears to be a local maximum and flow proceeds to stage 630. At stage 630, the height and width of the candidate point is determined by examining the points of inflection on either side of the candidate point.

At stage 640, if the peak, or candidate point, has a height greater than a minimum height and a width greater than a minimum width, the candidate point is stored in a list or table as a characteristic peak at stage 650. In addition to the candidate point, the two inflection points may be stored as well, signifying the beginning, top, and end of the peak. The variance determined during the pre-processing stage may be used to automatically determine minimum height requirements. Minimum height may also be manually set. Minimum peak width may be manually set or may be automatically set based on instrument resolution.

At stage 660, the next point is selected until stage 510 is complete.

Figure 7:
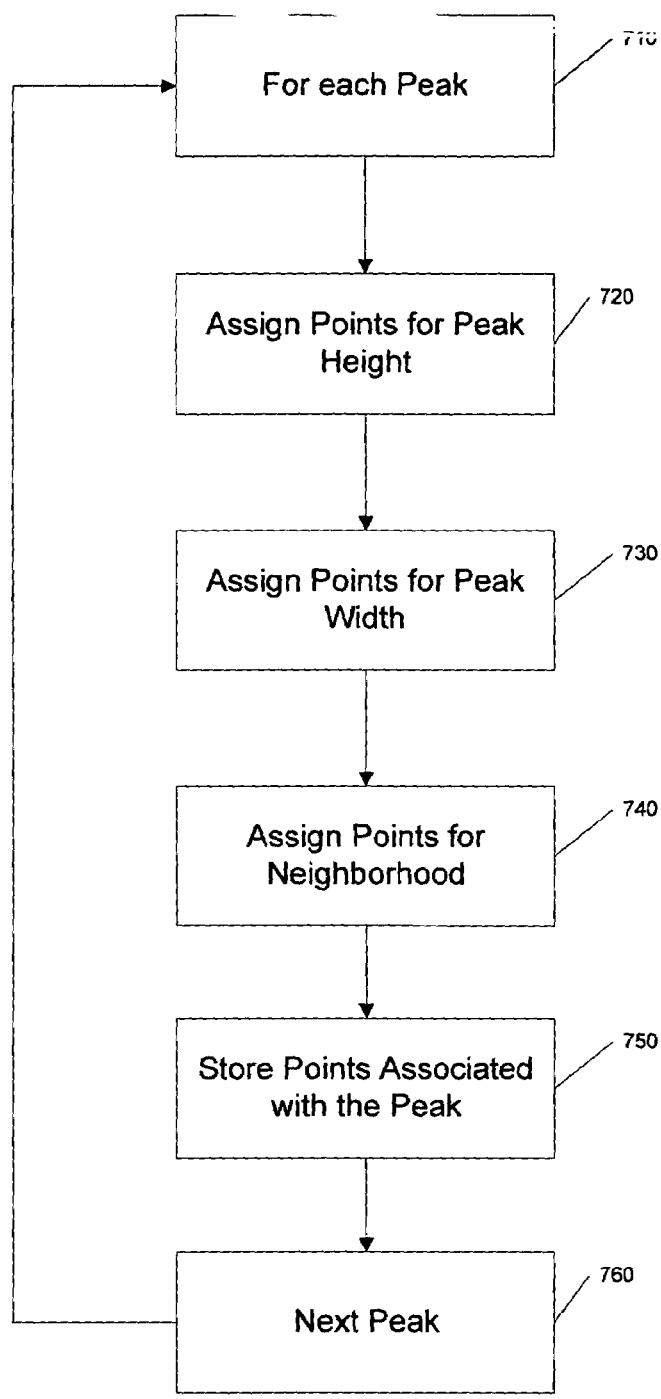
FIG. 7 is a flowchart of the probability assignment method consistent with the present invention.

FIG. 7 is a flowchart of the probability assignment method 520 consistent with the present invention. At stage 710, the processing begins and recurs through stages 720-760 until all desired characteristic peaks have been scored with a probability assignment. At stage 720, points are assigned to the peak based on the height of the peak. Scores may be assigned based on the multiple of threshold values of the height of the peak. The threshold value may be manually assigned or determined based on the previously computed variance (noise level). The threshold value may also be based on the presence of preferred orientation and particle statistics. For example, a peak that is five thresholds high may be given a height score of 50%. Conversely, a peak that does not meet a minimum height threshold multiple can incur a negative height score.

At stage 730, points are assigned to the peak based on the width of the peak. For example, for every 0.05 degree in width of the peak past a certain threshold, the width score may be given a +5%. So, in this example, a peak that is 1 degree wide may be given a width score of 100% [(1/0.05)=20×5%=100%]. Again, if the width is below a certain threshold a negative width score may be assigned.

At stage 740, points are assigned to the peak based on the neighborhood of the peak. For example, if there is nothing in the neighborhood of the peak, for example within 0.2 degrees, then the peak may be given a neighborhood score of +30%. If there is something on one side of the peak but not another, the peak may be given a neighborhood score of +15%. But, if the peak is in a crowded neighborhood, i.e. peaks on either side of the peak, the neighborhood score might be −30%.

As will be appreciated by those skilled in the art, various weightings and scores may be assigned to the height, width, and neighborhood scoring factors. Other peak characteristics may also be used for scoring.

At stage 750, the scores for the height, width, and neighborhood may be summed and stored in association with the peak in the characteristic peak list or table. At stage 760, the next characteristic peak is selected and analyzed through stages 710-750 until method 520 is complete. Then, flow proceeds to stage 530 (FIG. 5) for placing the characteristic peaks into groups based on the scores.

Figure 8:
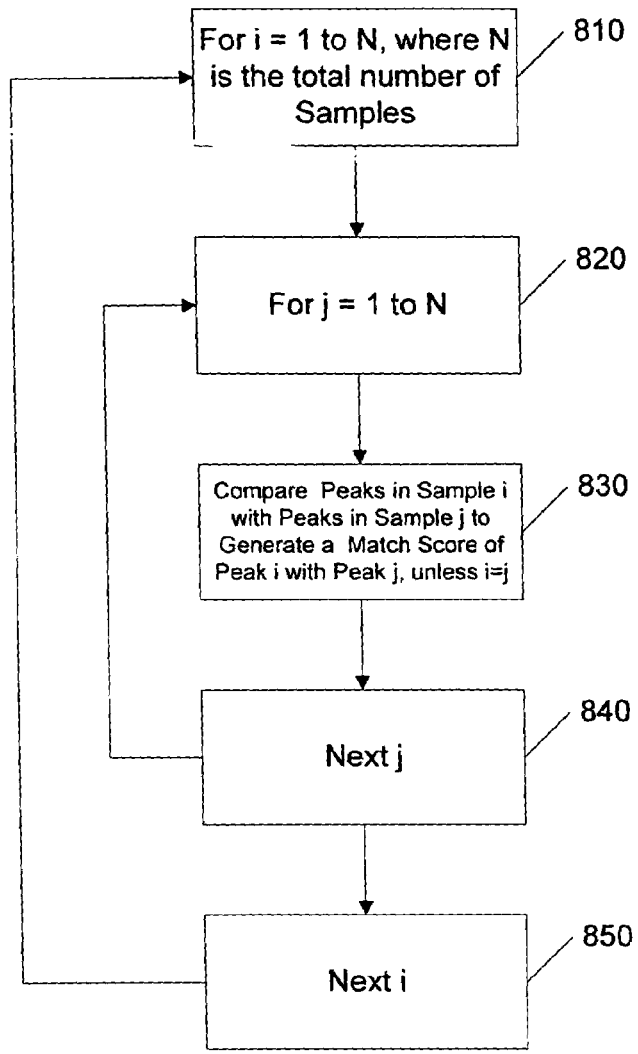
FIG. 8 is a flowchart of the peak pattern matching method consistent with the present invention.

FIG. 8 is a flowchart of the peak pattern matching method 330 consistent with the present invention. After receipt, optional pre-processing, and determining the characteristic peaks for all patterns upon which a user may want to run HCA, each pattern may be compared to other patterns to determine a similarity. Stages 810, 820, 840, and 850 operate to compare each pattern to every other pattern. Stage 830 performs the comparison by comparing each characteristic peak in Sample i with characteristic peaks in Sample j to look for matches. The result of the comparison is a similarity score.

Figure 9:
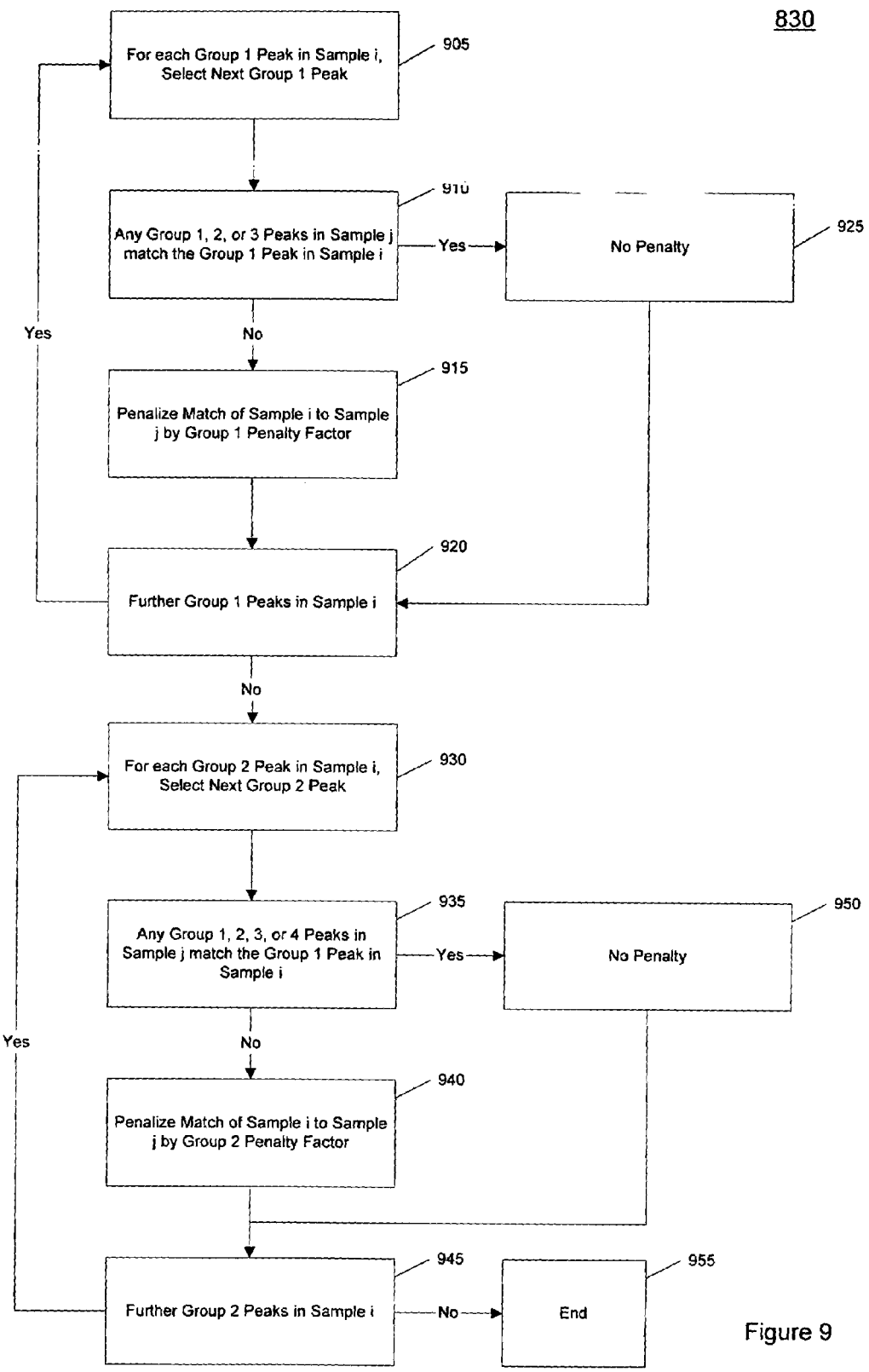
FIG. 9 is a flowchart of the peak comparison method consistent with the present invention.

FIG. 9 is a flowchart of the peak comparison method 830 consistent with the present invention. Consistent with the present invention, peak comparison method 830 compares the Group 1 and Group 2 peaks in Sample i, a first sample, to see if there are comparable characteristic peaks in Sample j, a second sample. Sample i Group 1 peaks may be found if there are corresponding Group 1, 2, or 3 characteristic peaks in Sample j. Sample i Group 2 peaks may be found if there are corresponding Group 1, 2, 3, or 4 peaks in Sample j. A corresponding peak is one at the same degree position along the X axis. The same degree position may range from tight, e.g. within 0.1 degree, to loose, e.g. within 1.5 degrees. This may be set automatically based on the resolution of the instrumentation or manually set. Where Group 1 peaks are missing, a first penalty for similarity may be applied. Where Group 2 peaks are missing, a second penalty for similarity may be applied. The penalties are totaled to yield a value representing the similarity between the patterns of Sample i and Sample j. A similarity of 0 would be a perfect match.

Stages 905-925 represent the analysis of Group 1 peak matching. Stages 930-950 represent the analysis of Group 2 peak matching. At stage 905, the first Group 1 peak of Sample i is selected. At stage 910, a check is made to determine if there are any Group 1, 2, or 3 peaks in Sample j that correspond to this peak of Sample i. If there is, at stage 925 no penalty is imposed and processing continues at stage 920 where the next Group 1 peak is selected. If there are no matching peaks. At stage 915, a penalty is imposed to the similarity score of Sample i to Sample j. This penalty may be, for example, 0.6. At stage 920, the next Group 1 peak is selected until all Group 1 peaks of Sample i are complete.

At stage 930, the first Group 2 peak of Sample i is selected. At stage 935, a check is made to determine if there are any Group 1, 2, 3, or 4 peaks in Sample j that correspond to this peak of Sample i. If there is, at stage 950 no penalty is imposed and processing continues at stage 945 where the next Group 2 peak is selected. If there are no matching peaks, at stage 940, a penalty is imposed to the similarity score of Sample i to Sample j. This penalty may be, for example, 0.3. At stage 945, the next Group 2 peak is selected until all Group 2 peaks of Sample i are complete. Method 830 ends at stage 955.

During peak comparison, the algorithm may treat overlapped peaks, split peaks (two peaks having been bifurcated into two peaks with a depression in between) and shoulder peaks (a first greater peak having a second lesser peak sprouting prior to the first peak's true inflection point), as multiple peaks if they are present in more than one pattern. If one pattern exhibits a split peak and one pattern exhibits a peak with a shoulder at the same position, they may be matched.

In addition, the peak matching algorithm may ignore, and choose not to perform matching, on high angle (high 2Theta) Group 2 peaks. For example, the 2Theta cutoff point may be determined by the equation, 2Theta_Cut_Off=2.0*asin (5.0*sin (2Theta_1/2.0)), where 2Theta_1 is the measured 2Theta angle of the lowest angle diffraction peak.

In addition, the algorithm may detect and flag missing families of peaks with common 'd' values, indicating the possible presence of preferred orientation. If such peaks are detected they may be included in the pattern matching as if they were physically present in the pattern. If a peak is missing at a particular 2Theta value, then the program looks for missing peaks at 2Theta values given by 2 asin (2Theta n/2) where n takes the values 1, 2, 3, 4.

A user may intervene in the method 830 to X-shift by a real number of degrees forward or backward to attempt to better align patterns for matching. X-shifting may be necessitated by instrumentation errors or variations. The method 830 may also be set to automatically perform some X-shifting to look for a better match, for example, if the algorithm determines that there is a constant X-shift between the peaks of the two patterns.

The resulting scores are used in the HCA described with reference to HCA method 240. Notice that method 830 yields scores of 0.0 to infinity, where 0.0 denotes a perfect match. Prior to the HCA the similarity scores are all scaled from 1.0 to 0.0, where 1.0 denotes a perfect match. Initially, HCA defines every pattern as a separate cluster. The two most similar clusters are aggregated into a cluster. The clustering then repeats until all clusters are joined together. The resulting clustering is displayed in a tree structure, known as a dendrogram. FIGS. 23a and 23b, to be discussed later, illustrate an exemplary dendrogram. The vertical axis displays each sample. Patterns that are similar clustered together toward the left portion of the horizontal axis. As similarity diverges, the clusters are grouped together toward the right portion of the horizontal axis. Thus, moving from left to right, the horizontal axis displays lesser degrees of similarity.

HCA stage 240 may provide a form bar, a vertical line that intersects a number of branches of the tree, where each intersected bar represents a form. Thus, the form bar segments the dendrogram into a number of clusters, where the number of clusters or forms will vary depending on the horizontal positioning of the form bar. HCA stage 240 may select an optimum position for the form bar based on the similarities determined in stage 230. Those skilled in the art will appreciate that many other types of user interfaces for segmenting the dendrogram into clusters can be envisioned.

FIG. 16 is an illustration of the smoothed, baseline corrected diffraction pattern with the peaks detected and categorized according to methods consistent with the present invention. Smoothed, baseline corrected pattern 1510 has been broken down into characteristic peaks categorized in groups. Group 1 characteristic peaks 1610 are the largest peaks in the pattern and carry the most weight in matching. Group 2 characteristic peaks 1620 are standard peaks in the pattern and carry less weight.

Figure 20:
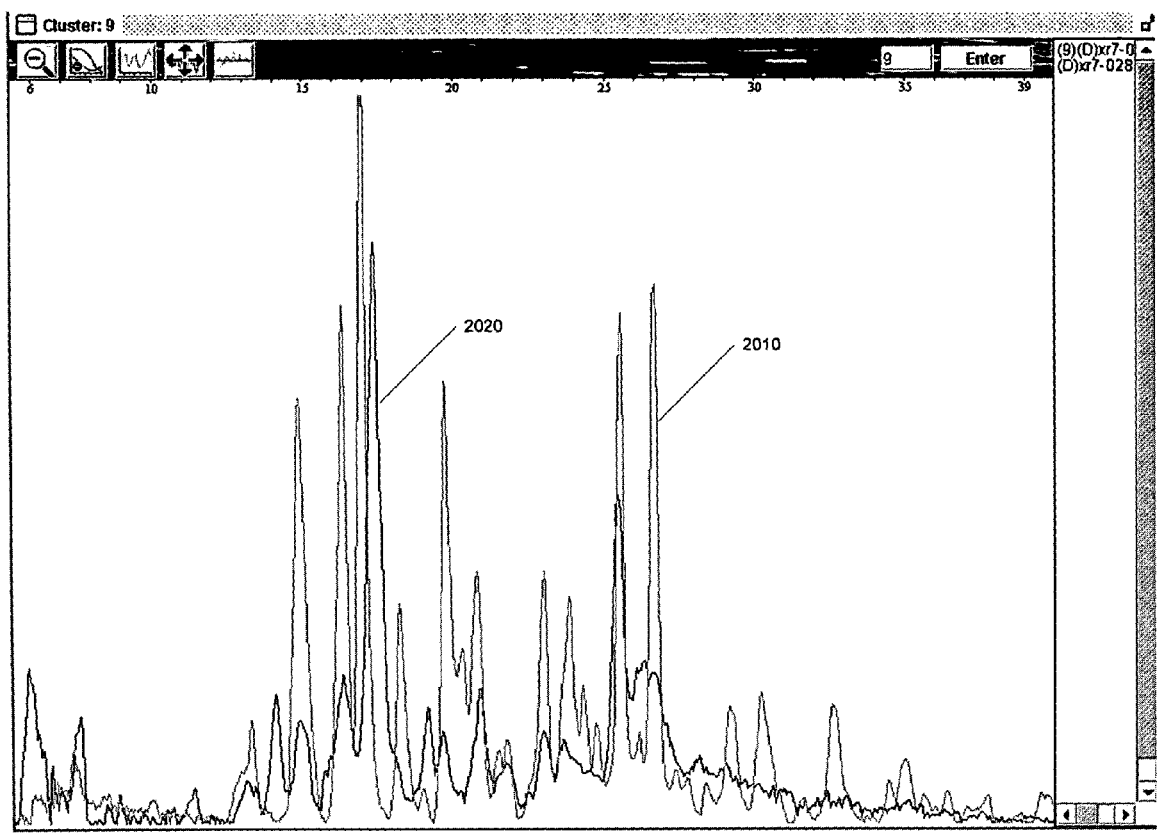
FIG. 20 is an illustration of the first smoothed, baseline corrected diffraction pattern compared to a second smoothed, baseline corrected diffraction pattern consistent with the present invention.

FIG. 20 is an illustration of the first smoothed, baseline corrected diffraction pattern compared to a second smoothed, baseline corrected diffraction pattern consistent with the present invention. Some of the peaks of the first pattern are missing from the second pattern, and some of the peaks of the second pattern are missing from the first pattern.

Figure 21:
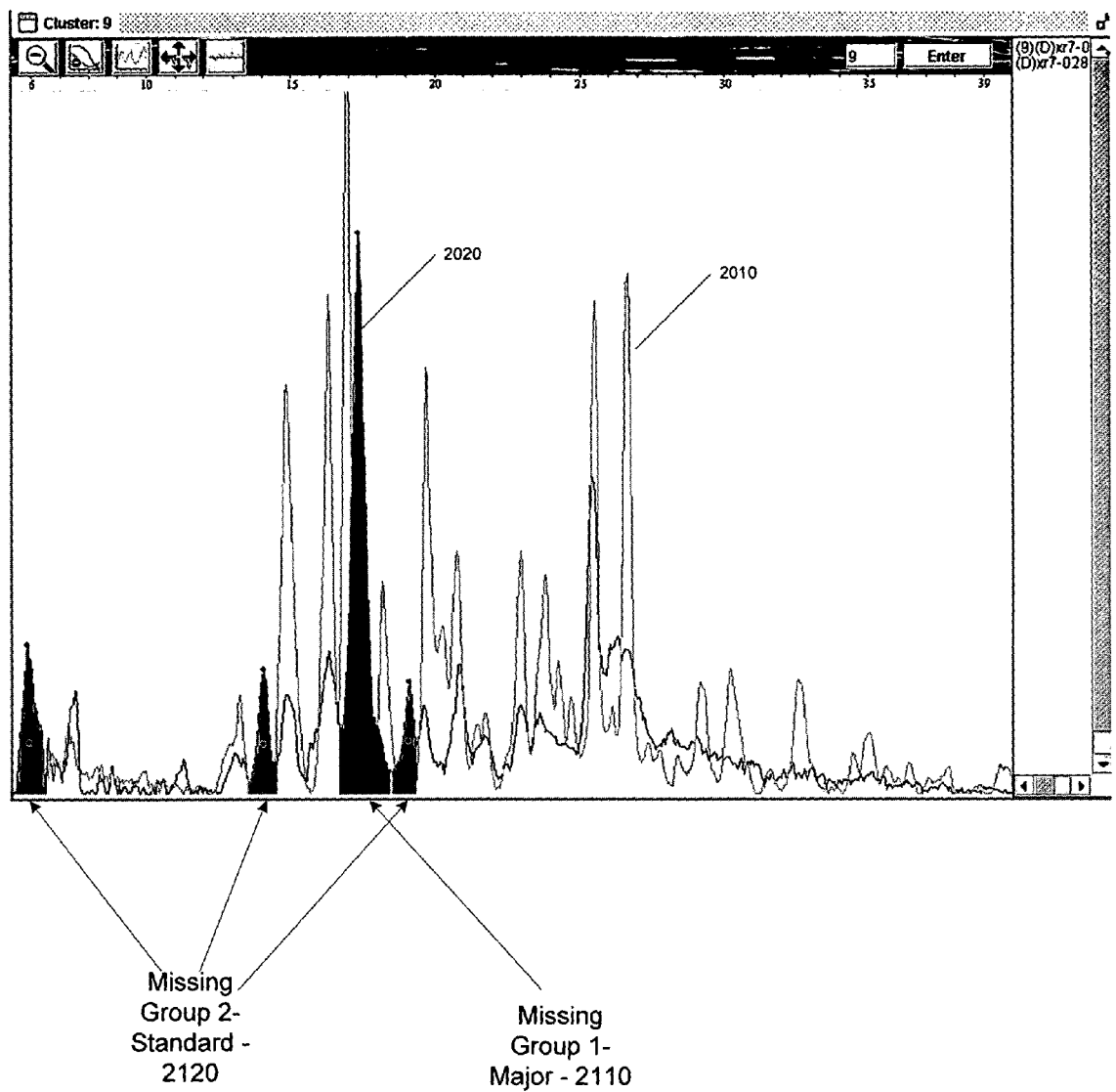
FIG. 21 is an illustration of the missing Group 1 and Group 2 peaks found in the first smoothed, baseline corrected diffraction pattern but missing in the second smoothed, baseline corrected diffraction pattern consistent with the present invention.

FIG. 21 is an illustration of the missing Group 1 and Group 2 peaks found in the first smoothed, baseline corrected diffraction pattern but missing in the second smoothed, baseline corrected diffraction pattern consistent with the present invention. There is a single missing Group 1 major peaks 2110 which would cause a 0.66 penalty to the similarity score. There are three missing Group 2 standard peaks 2120 which would cause a penalty of 0.9 (0.3×3). This would result in a total similarity of 1.56 of the first compared to the second.

Figure 22:
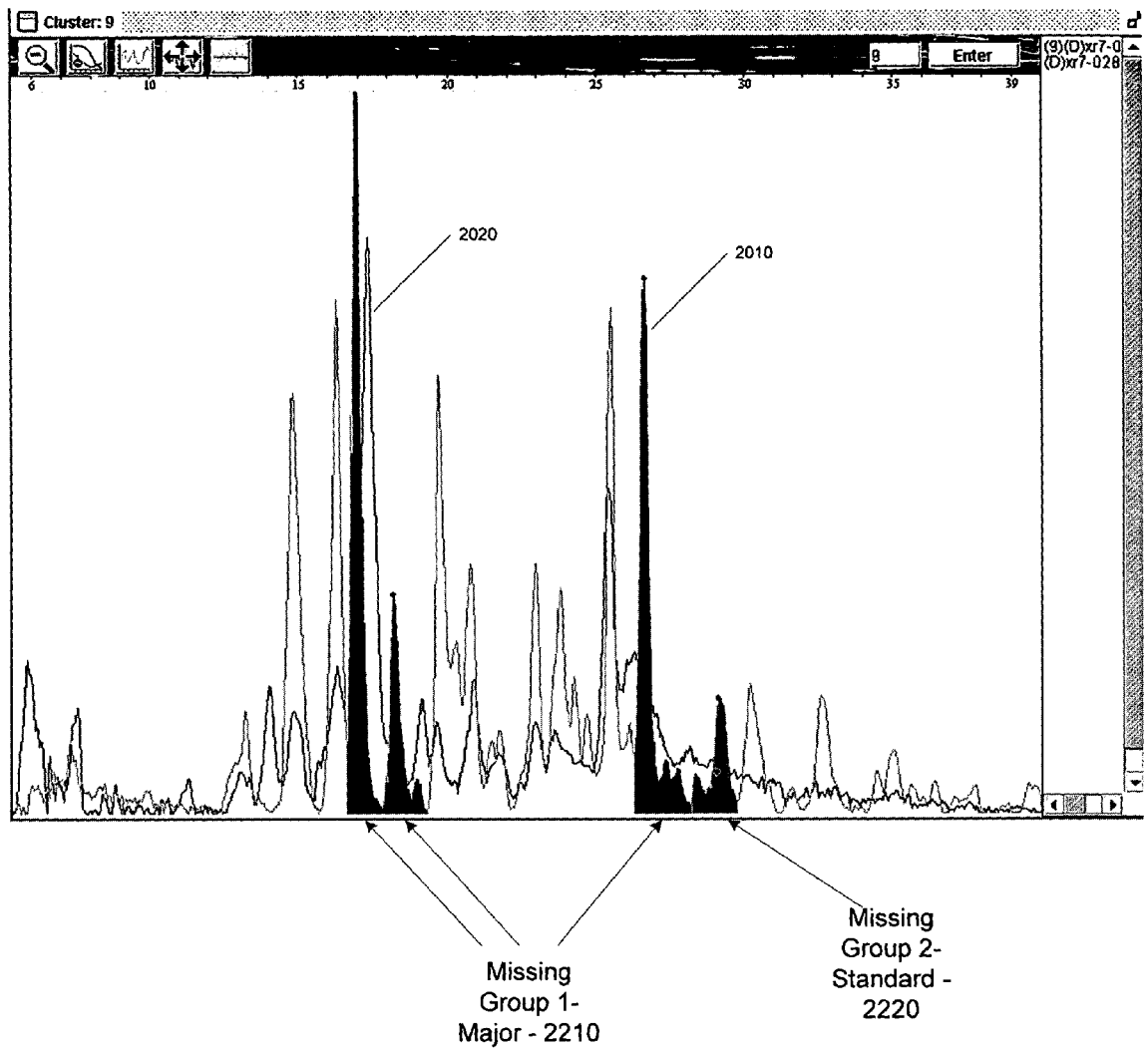
FIG. 22 is an illustration of the missing Group 1 and Group 2 peaks found in the second smoothed, baseline corrected diffraction pattern but missing in the first smoothed, baseline corrected diffraction pattern consistent with the present invention.

FIG. 22 is an illustration of the missing Group 1 and Group 2 peaks found in the second smoothed, baseline corrected diffraction pattern but missing in the first smoothed, baseline corrected diffraction pattern consistent with the present invention. There are three missing Group 1 major peaks 2210 which would cause a 1.98 (0.66×3) penalty to the similarity score. There is one missing Group 2 standard peak 2220 which would cause a penalty of 0.3 This would result in a total similarity of 2.28 of the second compared to the first. If these similarity scores are totaled, the total two-way similarity would be 2.28+1.56=3.84.

As previously mentioned, peak matching is useful for identifying similar unit cells and crystal symmetry. However, intensity envelope matching is useful for identifying isostructures of the crystalline forms and clustering disordered forms with ordered forms.

Figure 24:
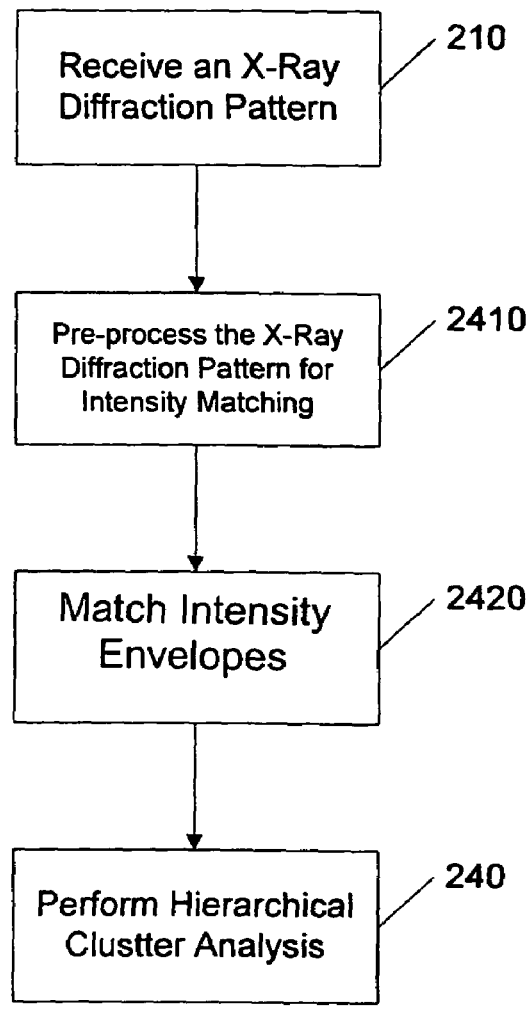
FIG. 24 is a flowchart of the operation of the intensity envelope comparison methodology of the Analysis System consistent with the present invention.

FIG. 24 is a flowchart of the operation of the intensity envelope comparison methodology of the Analysis System consistent with the present invention. At stage 210, a pattern is received as previously described. At stage 2410, the pattern may be pre-processed. Pre-processing the pattern may comprise one or more of: scaling the pattern into a common measurement range; scaling the pattern into a common step size; normalizing the pattern; and smoothing the pattern. Intensity envelope pre-processing stage 2410 is further explained with reference to FIG. 25 that follows. At stage 2530, the intensity envelope of the pattern may be compared to the intensity envelopes of the other sample patterns. The result of stage 2530 may be a measure of the similarity between the pattern and other patterns. Finally, as previously described, the similarity measure of the patterns is used to perform HCA analysis at stage 240.

Figure 25:
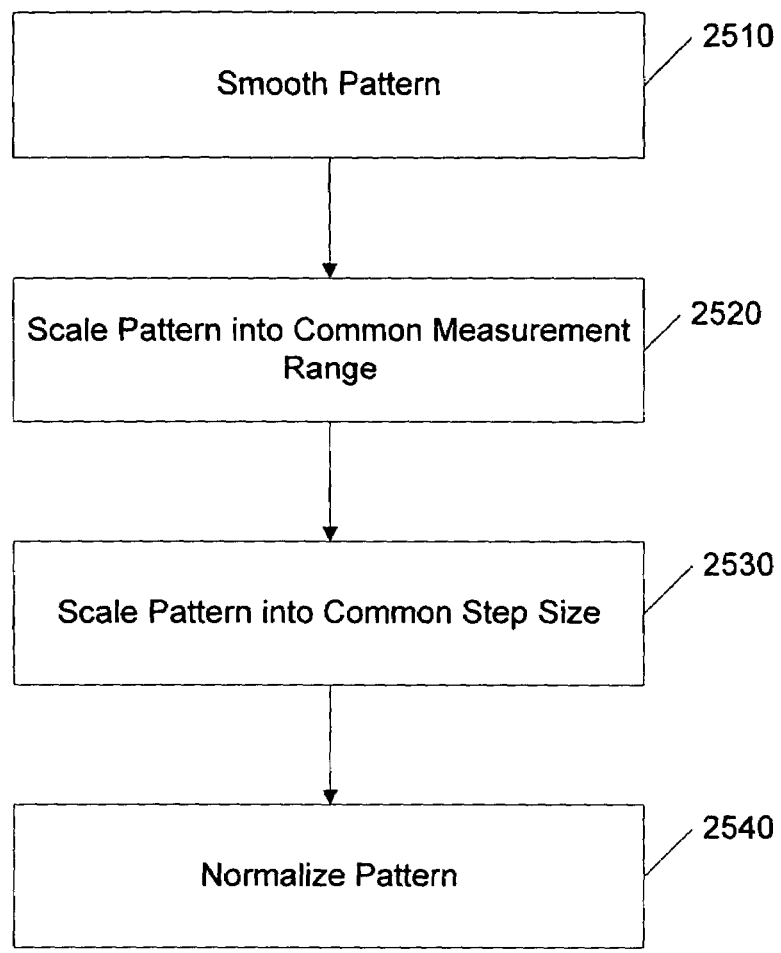
FIG. 25 is a flowchart of the operation of the intensity envelope comparison pre-processing methodology consistent with the present invention.

FIG. 25 is a flowchart of the operation of the intensity envelope comparison pre-processing methodology 2410 consistent with the present invention. At stage 2510, the pattern may be smoothed. At stage 2520, the pattern is processed to be in a common measurement range with the other patterns. At stage 2530, the pattern is processed to be a common step size. Instrumentation may vary in step size, for example one instrument may be 0.02 degrees and another instrument 0.05 degrees. At stage 2540, the pattern is normalized. In this stage the weight, or integrated intensity, is normalized or standardized across all patterns.

Figure 26:
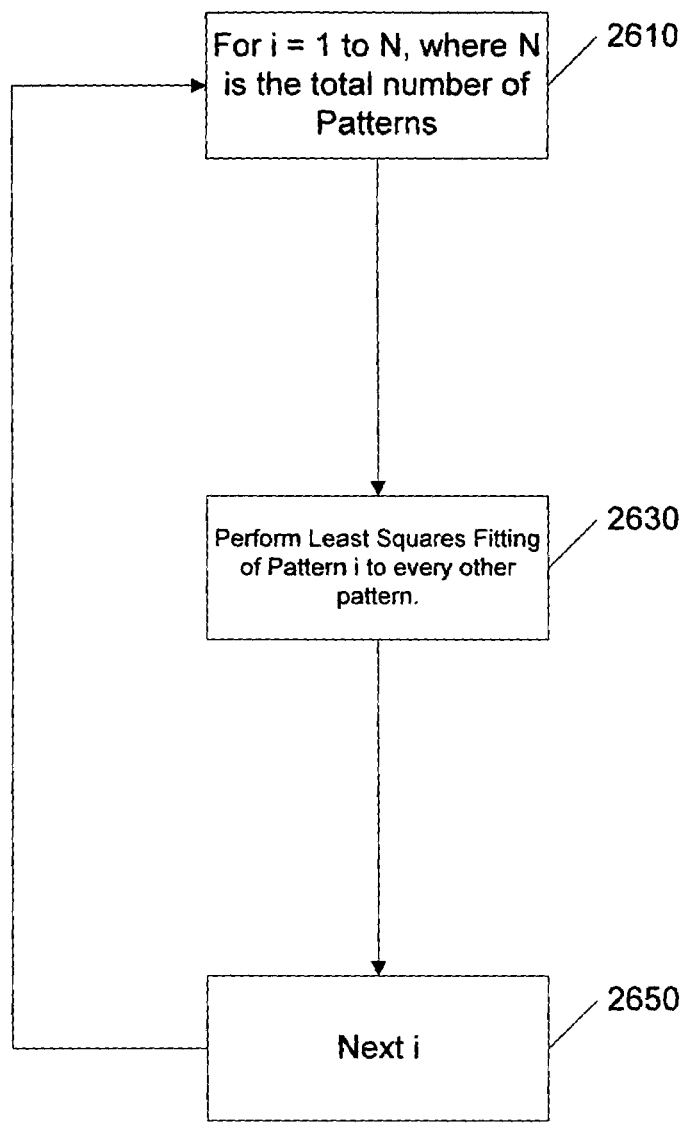
FIG. 26 is a flowchart of the intensity matching method consistent with the present invention.

FIG. 26 is a flowchart of the intensity matching method 2420 consistent with the present invention. After receipt and pre-processing, each pattern may be compared to all other patterns to determine a similarity based on the intensity envelope. Stages 2610, 2630, and 2650 operate to compare each pattern with all other patterns. Stage 2630 performs the comparison by comparing the general intensity envelope of Sample i with the general intensity envelope of all other samples, Samples 1 to N where N is the number of samples, using a least squares fitting algorithm. The results of the comparison are a percentage score of each sample of Samples 1 to N present in Sample i. As previously described, the similarity score is used in the HCA stage 240.

Figure 27:
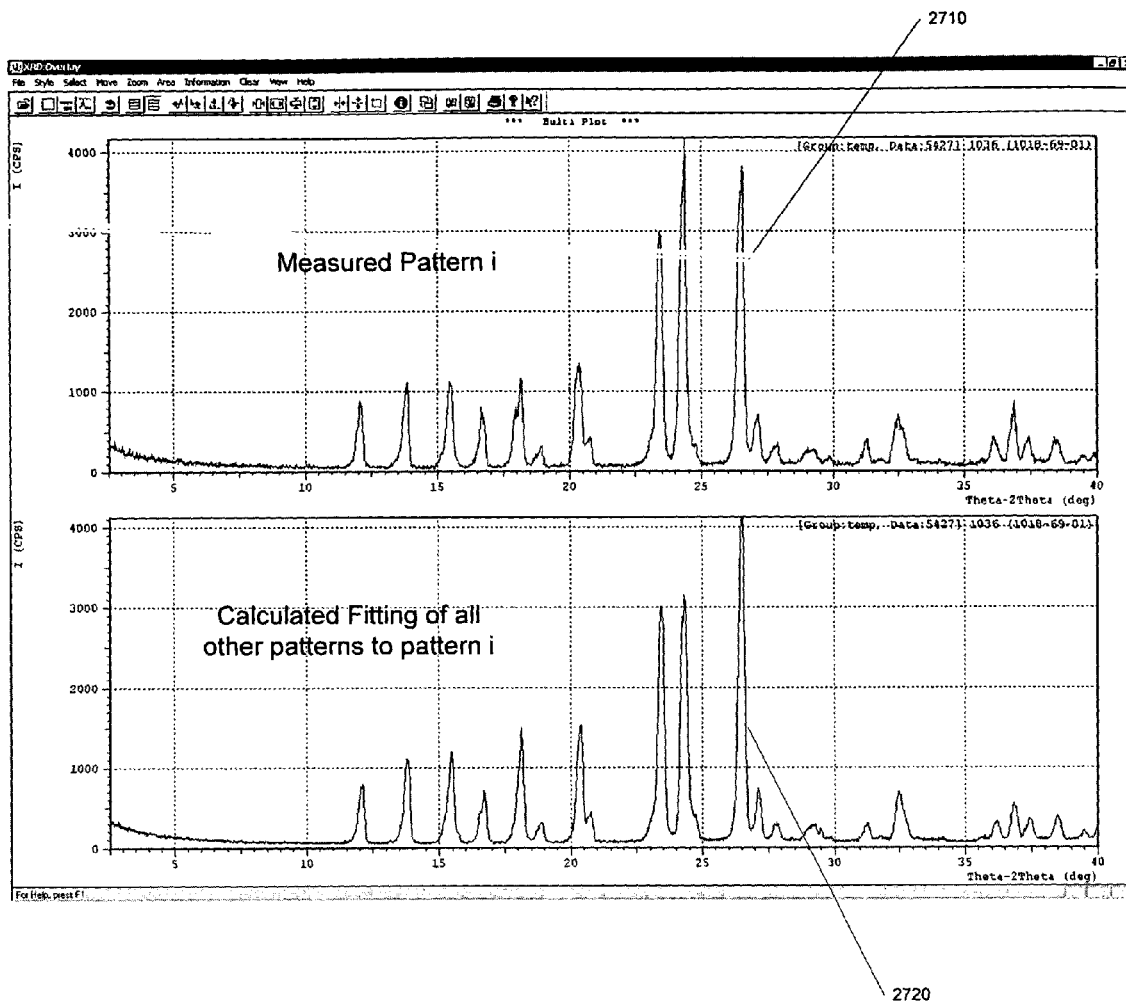
FIG. 27 is a graph of a sample diffraction pattern and a calculated pattern resulting from the least squares fitting of all other patterns consistent with the present invention.

FIG. 27 is a graph of a measured diffraction pattern 2710 and a calculated pattern 2720 resulting from the least squares fitting of all other patterns consistent with the present invention. The measured pattern 2710 has been pre-processed to normalize the patterns for comparison.

Figure 28:
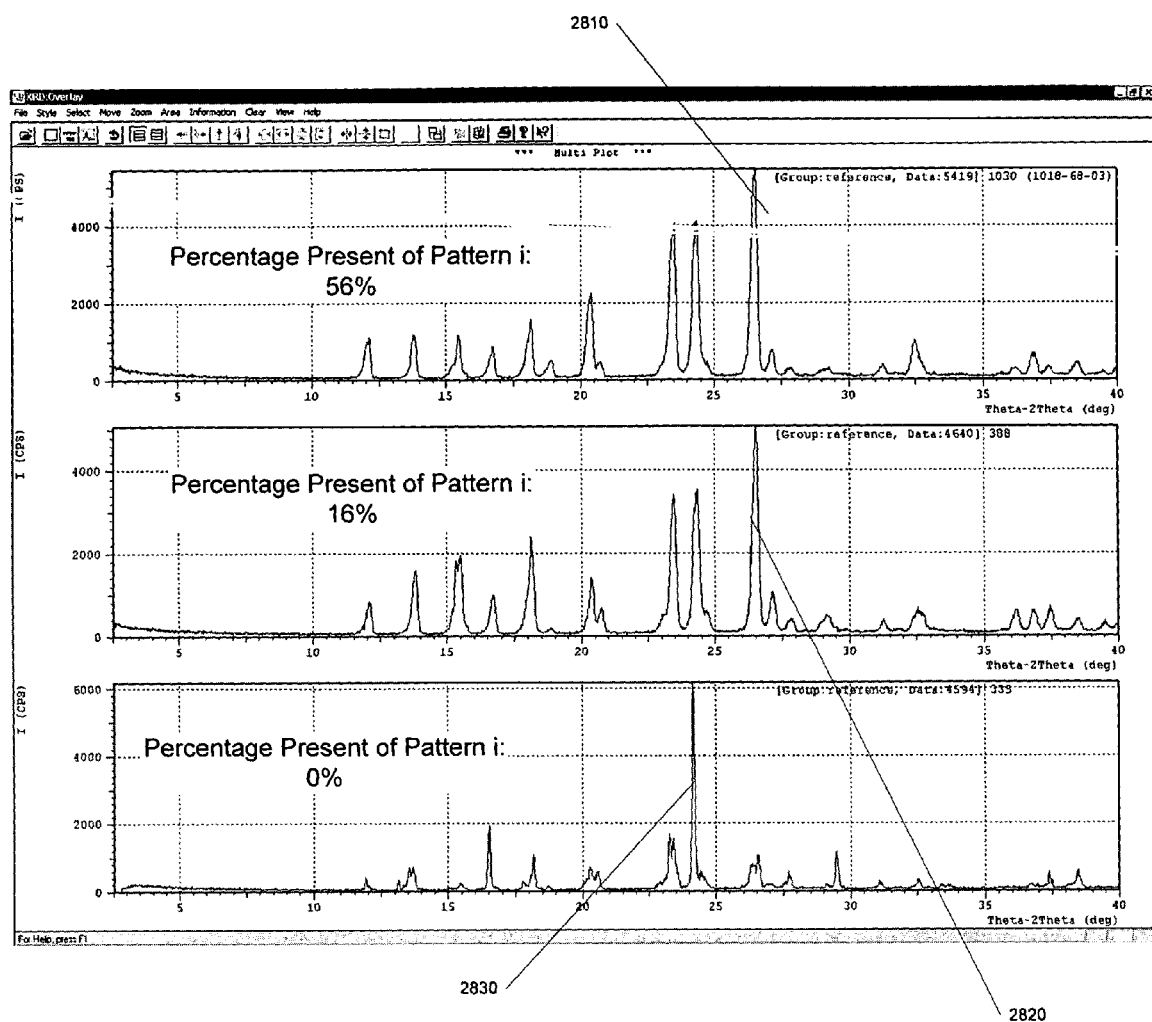
FIG. 28 is a graph of a plurality of diffraction patterns analyzed according to the intensity envelope comparison method and the resulting least squares analysis consistent with the present invention.

FIG. 28 is a graph of a plurality of diffraction patterns analyzed according to the intensity envelope comparison method and the resulting least squares analysis consistent with the present invention. Pattern 2810 matches pattern 2710 with a similarity of 56%; pattern 2820 matches pattern 2710 with a similarity of 16%; and pattern 2830 matches pattern 2710 with a similarity of 0%. These similarity scores may be used for HCA to form clusters as previously described.

In addition, a similar method may be utilized to perform quantitative analysis of samples containing either mixed crystalline phases or mixed crystalline and disordered phases. The quantification of mixed crystalline and disordered phases is called percentage crystallinity analysis; For example, a diffraction pattern from a mixture will contain within it the diffraction patterns corresponding to each of the phases present in the mixture. Utilizing the above methodology, the presence, by percent weight, of each of the phases within the mixture may be analyzed and represented as a weight percent similar to the representation of the above similarity percentage. In addition, disordered forms, generated as described below, may be presented to the above algorithm for the analysis of the percent crystallinity.

Prior art methods may fail to match forms if there is significant disorder present. In other words, forms that should be clustered together may be clustered apart because of disorder. In order to match crystalline forms that are disordered, a disorder simulation algorithm has been developed to simulate disorder forms that may be compared to measured patterns to identify relationships. Through this method, disordered crystalline or polymorph forms may be matched with more ordered crystalline or polymorph forms.

Figure 29:
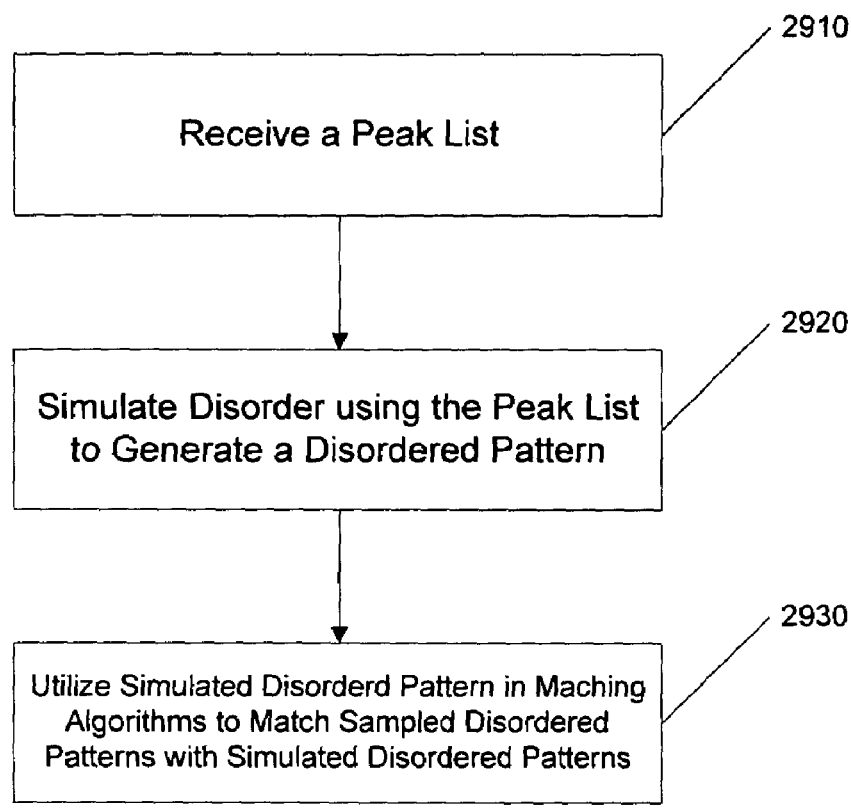
FIG. 29 illustrates a disorder simulation algorithm consistent with the principles of the present invention.

FIG. 29 illustrates a disorder simulation algorithm 2900 consistent with the principles of the present invention. At stage 2910, a peak list, as previously described, is received where the peak list may be from a known, ordered, crystalline form. The peak list may be imported as a data file or generated from the previously described pattern matching algorithms, for example, as described with reference to FIG. 6. An operation may also manually enter the peak list.

In addition, disorder simulation algorithm 2900 may calculate and generate a peak list based on a known crystal structure. For calculated patterns, algorithm 2900 may apply a Lorentz polarization factor to simulate the characteristics of a peak list generated by an X-Ray diffraction instrument. The Lorentz polarization factor may be selected based on the characteristics of the particular X-Ray diffraction instrument used to gather data from other patterns of interest. The Lorentz polarization factor may be applied to the peak list prior to further calculations.

An example of the use of the Lorentz polarization factor for Theta-2Theta scans using a Bragg-Brentano geometry without monochromator crystal may be:

$$LP = \frac{1 + \cos^2 2\vartheta}{\sin(\vartheta)\sin(2\vartheta)};$$

where 2Theta is the measurement angle of the diffraction pattern.

At stage 2920, the simulated disordered pattern is generated using the peak list. This will be discussed further with reference to FIG. 30.

At stage 2930, the simulated disordered pattern is compared to the measured patterns. This may be by using the previously described matching algorithms and incorporating the simulated disordered pattern into the matching or HCA engine, or by visual inspection (overlaying the simulated pattern over the measured pattern). By incorporating the simulated disordered pattern into the matching algorithms, measured disordered patterns can be grouped along with crystalline pattern forms, if that is desired, facilitating the work of the operator during a polymorph or salt screen.

Figure 30:
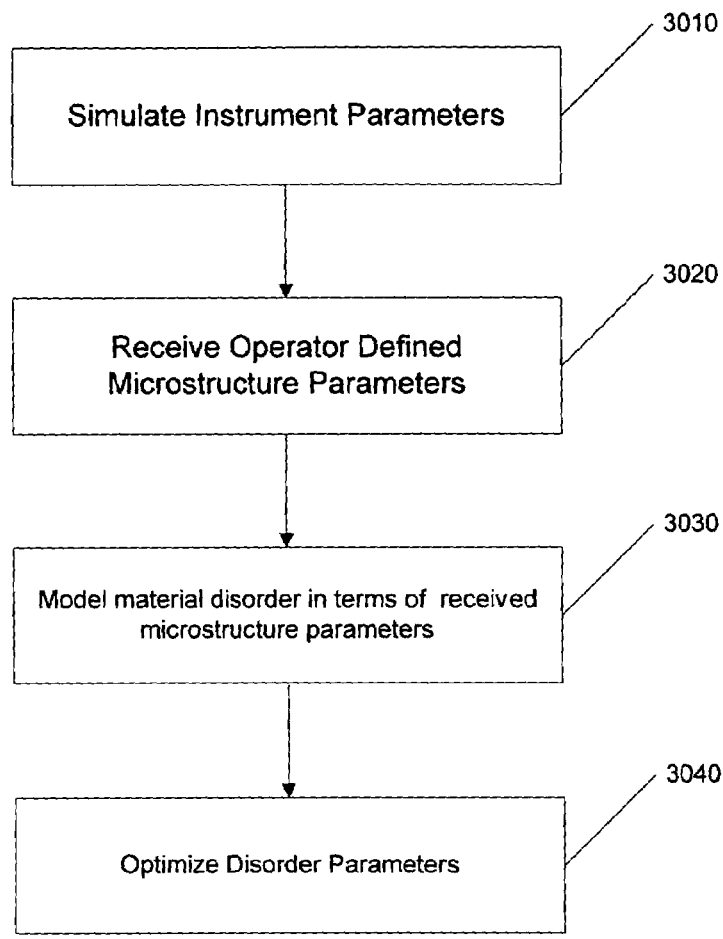
FIG. 30 illustrates a flowchart of the generation of the simulated disordered pattern from the received peak list.

FIG. 30 illustrates a flowchart of the generation of the simulated disordered pattern 2920 from the received peak list. At stage 3010, instrument parameters may be simulated. Because the simulated disordered patterns will be compared to measured patterns, stage 3010 may generate a crystalline pattern as measured by a selected instrument. The instrument function may be modeled by one or more parameters, for example, peak shape, background, and noise. The chosen peak shape may be a split Pseudo Voigt with independently variable asymmetry and weighting factors. Continuously variable power laws may model the peak width, asymmetry, and weighting factor, for example, as a function of 2Theta (the measurement angle). An exemplary form of the peak width parameter may make use of the well-known Cagliotti formula: Peak Full Width=SQRT (U tan (Theta) tan (Theta)+V tan (Theta)+W), where U is . . . , V is . . . , and W is . . . .

The asymmetry and Pseudo Voigt weighting factors may follow similar power laws as a function of 2Theta.

The noise parameter may make use, for example, of Poisson statistics where the noise distribution 1 sigma is the square root of the X-ray intensity at each point.

Simulation of the instrumental function may also make use of the spectral signature of the X-ray source. For a fixed tube or rotating anode system, this may imply the addition of a K-alpha 2 wavelength component to the simulated pattern. For synchrotron data, for example, this data may not be needed. The algorithm may utilize a table comprising one or more standard anode materials with their respective default K-alpha 1 and K-alpha 2 X-ray wavelengths.

At stage 3020, one or more operator defined microstructure parameters may be received. These parameters may include, for example: crystallite size, D, in Angstroms, typically between 500 and 20 Angstroms for example; microstrain, E, in percent, typically between 0.1% and 4% for example; thermal strain, alpha, in Angstroms, typically between 0.1 and 0.2 Angstroms for example; and residual strain, E, in Angstroms, typically between 0.1 and 0.2 Angstroms. During simulation at stage 3030, crystallite size and microstrain may cause broadening of the diffraction peak. Thermal strain may cause a 2Theta dependent dampening of the intensity, and residual strain may cause peak movement.

For each set of one or more of these input microstructure parameters, a disordered diffraction pattern may be simulated, where the simulation includes one or more instrumental factors.

At stage 3030, the material disorder is modeled based on the operator defined microstructure parameters received. Application of the microstructure parameters may be applied isotropically without knowledge of the underlying crystalline structure. As simulated patterns may be combined, it is possible that stage 2920 can be used to model complex anisotropic disorder through sequential calculations.

Crystal size may be modeled in terms of the Scherrer equation, well known to those skilled in the art.

$$PeakBroadening \text{ (radians)} = \frac{K\lambda}{D\cos(\vartheta)};$$

where K is the Scherrer constant (approximately 0.9), lambda is the X-ray wavelength in Angstroms, and D is the crystallite size in Angstroms.

Microstrain may be modeled, for example, using the strain component of the Williamson and Hall model.

PeakBroadening(radians)=$4E \tan(\theta)$

These two peak broadening parameters, crystal size and microstrain, may be combined with the instrument profile using a Gaussian approximation, for example:

$$FinalPeakWidth = \sqrt{H1H1 + H2H2 + H3H3};$$

where H1 is the instrumental profile previously described, H2 is the crystallite size profile, and H3 is the microstrain profile.

Thermal strain may be modeled, for example, by the Debye Waller thermal factor that damps the measured intensities preferentially at high 2Theta values. The form of the Debye Waller factor may be modified to represent random strain within the crystal unit cell.

$$DBWfactor = e^{-\left(\frac{4\pi\alpha\sin(\vartheta)}{\lambda}\right)^2}$$

Residual strain may cause peak movement. The form of the peak movement may be very similar to the microstrain peak broadening component.

PeakMovement(radians)=$-2E \tan(\theta)$

Figure 31:
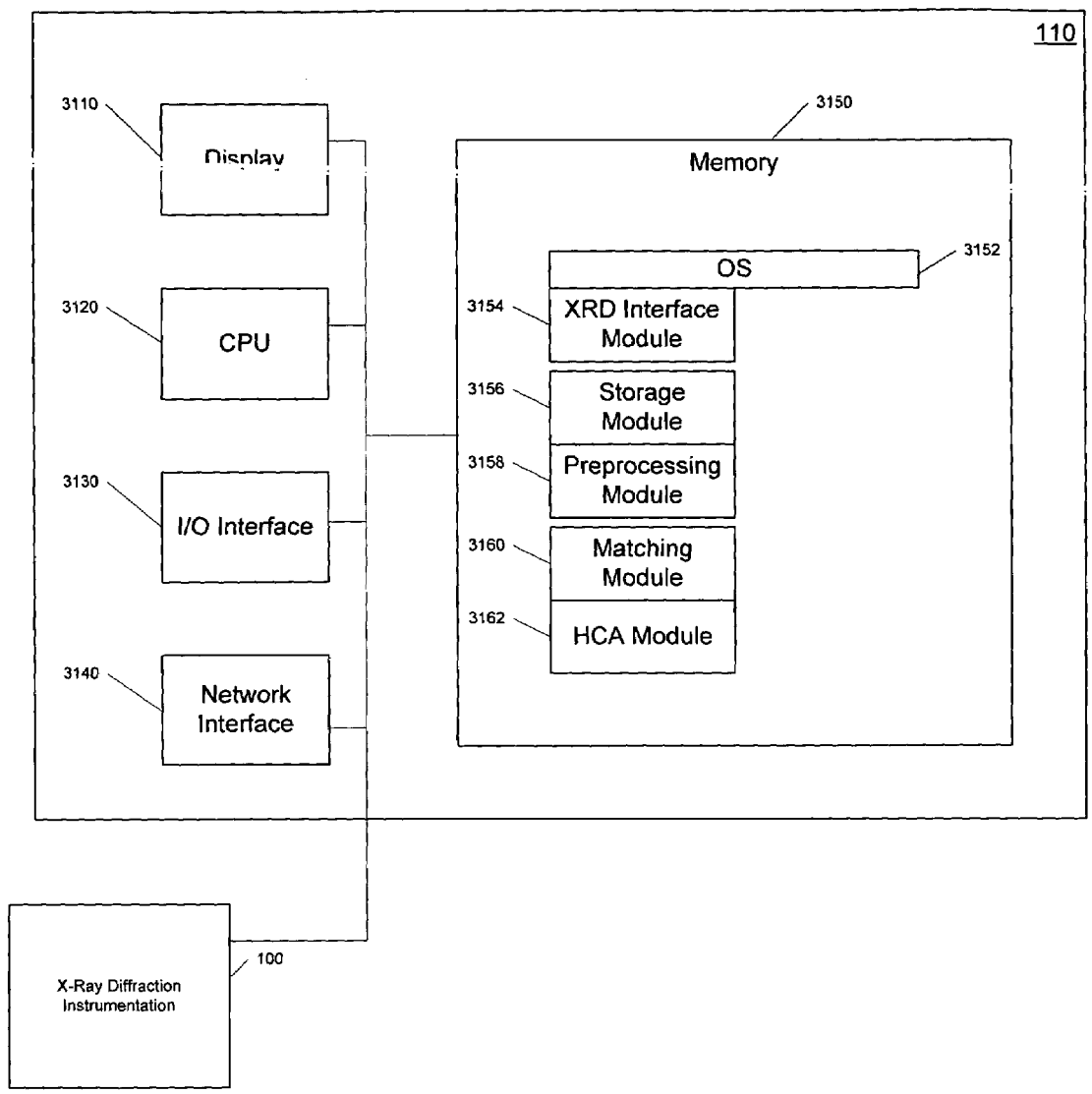
FIG. 31 is a block diagram of an Analysis System consistent with the present invention.

FIG. 31 is a block diagram of an Analysis System 110 consistent with the present invention. As illustrated in FIG. 31, a system environment of an Analysis System 110 may include a display 3110, a central processing unit 3120, an input/output interface 3130, a network interface 3140 and memory 3150 coupled together by a bus. Analysis System 110 is adapted to include the functionality and computing capabilities to receive diffraction data from Instrumentation 100 and to pre-process the diffraction data, match the diffraction data between samples, and perform HCA on the results of the sample matching scores. The input, output, and monitoring of the system may be provided on display 3110 for viewing.

As shown in FIG. 31, Analysis System 110 may comprise a PC or mainframe computer for performing various functions and operations consistent with the invention. Analysis System 110 may be implemented, for example, by a general purpose computer selectively activated or reconfigured by a computer program stored in the computer, or may be a specially constructed computing platform for carrying-out the features and operations of the present invention. Analysis System 110 may also be implemented or provided with a wide variety of components or subsystems including, for example, one or more of the following: one or more central processing units 3120, a co-processor, memory 3150, registers, and other data processing devices and subsystems. Analysis System 110 may also communicate or transfer XRD sample data, matching scores, HCA results or other data via I/O interface 3130 and/or network interface 3140 through the use of direct connections or communication links to other elements of the present invention. For example, a firewall in network interface 3140 prevents access to the platform by unpermitted outside sources.

Alternatively, communication within Analysis System 110 can be achieved through the use of a network architecture (not shown). In the alternative embodiment (not shown), the network architecture may comprise, alone or in any suitable combination, a telephone-based network (such as a PBX or POTS), a local area network (LAN), a wide area network (WAN), a dedicated intranet, and/or the Internet. Further, it may comprise any suitable combination of wired and/or wireless components and systems. By using dedicated communication links or shared network architecture, Analysis System 110 may be located in the same location or at a geographically distant location from Instrumentation 100.

I/O interface 3130 of the system environment shown in FIG. 31 may be implemented with a wide variety of devices to receive and/or provide the data to and from Analysis System 110. I/O interface 3130 may include an input device, a storage device, and/or a network. The input device may include a keyboard, a mouse, a disk drive, video camera, magnetic card reader, or any other suitable input device for providing data to Analysis System 110.

Network interface 3140 may be connected to a network, such as a Wide Area Network, a Local Area Network, or the Internet for providing read/write access to records.

Memory device 3150 may be implemented with various forms of memory or storage devices, such as read-only memory (ROM) devices and random access memory (RAM) devices. Memory device 3150 may also include a memory tape or disk drive for reading and providing records on a storage tape or disk as input to Analysis System 110. Memory device 3150 may comprise computer instructions forming: an operating system 3152 and one or more modules 3154, 3156, 3158, 3160, and 3162.

As previously illustrated, patterns and dendrograms may be produced by the present invention. To facilitate user interaction with the system, a set of user tools may be provided consistent with the present invention. Patterns may be shifted in the X or Y directions, or combinations thereof. The patterns may be manually shifted into different clusters or resorted. In addition, as previously mentioned, the user may slice the Dendrogram in various ways to change the number of forms selected. In addition, a mixture tools permits the user to select a series of reference patterns and analyze other patterns to determine if it is a mixture of the reference patterns.

Also, a user may subtract a first pattern from a second pattern, wherein the subtraction of the pattern occurs by the subtraction of like peaks, regardless of the peak size. For example, subtracting pattern A from pattern B, each of which has characteristic peaks of varying amplitudes at 2Theta=i, will result in a complete subtraction of the peak to a zero level regardless of the actual amplitude differences. The resulting pattern from the above subtraction operation may be utilized as an input pattern in matching or HCA operations.

Those skilled in the art will appreciate that all or part of systems and methods consistent with the present invention may be stored on or read from other machine-readable media, such as: secondary storage devices, like hard disks, floppy disks, and CD-ROM; a carrier wave received from the Internet; or other forms of machine-readable memory, such as read-only memory (ROM) or random-access memory (RAM).

Furthermore, one skilled in the art will also realize that the processes illustrated in this description may be implemented in a variety of ways and include multiple other modules, programs, applications, scripts, processes, threads, or code sections that all functionally interrelate with each other to accomplish the individual tasks described above for each module, script, and daemon. For example, it is contemplated that these programs modules may be implemented using commercially available software tools, using custom object-oriented code written in the C++ programming language, using applets written in the Java programming language, or may be implemented as with discrete electrical components or as one or more hardwired application specific integrated circuits (ASIC) custom designed just for this purpose.

It will be readily apparent to those skilled in this art that various changes and modifications of an obvious nature may be made, and all such changes and modifications are considered to fall within the scope of the appended claims. Other embodiments of the invention will be apparent to those skilled in the art from consideration of the specification and practice of the invention disclosed herein. It is intended that the specification and examples be considered as exemplary only, with a true scope and spirit of the invention being indicated by the following claims and their equivalents.

What is claimed is:

1. A method of analyzing patterns, comprising:
   receiving a first diffraction pattern;
   receiving a second diffraction pattern;
   receiving a third diffraction pattern;
   detecting the characteristic peaks of the first diffraction pattern;
   detecting the characteristic peaks of the second diffraction pattern;
   detecting the characteristic peaks of the third diffraction pattern;
   determining a first similarity between the first and the second diffraction patterns based on the characteristic peaks of the first and the second diffraction patterns;
   determining a second similarity between the first and the third diffraction patterns based on the characteristic peaks of the first and the third diffraction patterns;
   determining a third similarity between the second and the third diffraction patterns based on the characteristic peaks of the second and the third diffraction patterns;
   performing hierarchical cluster analysis on the first, the second, and the third diffraction pattern based on the determined first, second, and third similarity; and
   displaying the results of the hierarchical cluster analysis;
   wherein the characteristic peaks are detected by computing the variance of the diffraction patterns.

2. A method of analyzing patterns, comprising:
   receiving a first diffraction pattern;
   receiving a second diffraction pattern;
   receiving a third diffraction pattern;
   detecting the characteristic peaks of the first diffraction pattern;
   detecting the characteristic peaks of the second diffraction pattern;
   detecting the characteristic peaks of the third diffraction pattern;
   determining a first similarity between the first and the second diffraction patterns based on the characteristic peaks of the first and the second diffraction patterns;
   determining a second similarity between the first and the third diffraction patterns based on the characteristic peaks of the first and the third diffraction patterns;
   determining a third similarity between the second and the third diffraction patterns based on the characteristic peaks of the second and the third diffraction patterns;
   performing hierarchical cluster analysis on the first, the second, and the third diffraction pattern based on the determined first, the second, and the third similarity; and
   displaying the results of the hierarchical cluster analysis;
   wherein the characteristic peaks are detected by a method comprising:
      determining the peaks of the diffraction patterns; and
      assigning probability scores to the determined peaks of the diffraction pattern.

3. The method of claim 2, wherein the results of the hierarchical cluster analysis are displayed as a dendrogram.

4. The method of claim 2, wherein the characteristic peaks are detected by computing the variance of the diffraction patterns.

5. A method of analyzing patterns, comprising:
   receiving a first diffraction pattern;
   receiving a second diffraction pattern;
   detecting the characteristic peaks of the first diffraction pattern;
   detecting the characteristic peaks of the second diffraction pattern;
   determining a similarity between the first and the second diffraction patterns based on the characteristic peaks of the first and the second diffraction patterns;
   performing hierarchical cluster analysis on the first and second diffraction pattern based on the determined similarity; and
   displaying the results of the hierarchical cluster analysis;
   wherein the characteristic peaks are detected by a method comprising:
      determining the peaks of the diffraction patterns; and
      assigning probability scores to the determined peaks of the diffraction pattern; and
   wherein the method of analyzing patterns further comprises discretely allocating the detected characteristic peaks into one or more groups based on the assigned probability scores.

6. The method of claim 5, wherein discretely allocating the detected characteristic peaks comprises discretely allocating the determined characteristic peaks into one or more groups based on the assigned probability scores.

7. The method of claims 5 or 6, wherein discretely allocating the characteristic peaks comprises discretely allocating the characteristic peaks into a first, a second, a third, and a fourth group based on the assigned probability scores.

8. The method of claim 7, wherein determining the similarities based on the characteristic peaks comprises comparing one or more characteristic peaks in the first diffraction pattern with one or more characteristic peaks in the second diffraction pattern.

9. The method of claim 8, wherein comparing one or more characteristic peaks in the first diffraction pattern with one or more characteristic peaks in the second diffraction pattern further comprises:
for each characteristic peak in the first group of the first diffraction pattern, comparing the characteristic peak in the first group of the first diffraction pattern with the characteristic peaks in the first, second, or third group of the second diffraction pattern and penalizing a matching score if the characteristic peak in the first group of the first diffraction pattern is not found in the first, second, or third group of the second diffraction pattern.

10. The method of claim 9, wherein comparing one or more characteristic peaks in the first diffraction pattern with one or more characteristic peaks in the second diffraction pattern further comprises:
for each characteristic peak in the second group of the first diffraction pattern, comparing the characteristic peak in the second group of the first diffraction pattern with the characteristic peaks in the first, second, third, or fourth group of the second diffraction pattern and penalizing a matching score if the characteristic peak in the first group of the first diffraction pattern is not found in the first, second, third, or fourth group of the second diffraction pattern.

11. The method of claim 8, wherein determining the similarities based on the characteristic peaks further comprises matching the diffraction patterns based on the characteristic peaks, wherein matching the diffraction patterns based on the characteristic peaks further comprises comparing one or more characteristic peaks in a diffraction pattern with one or more characteristic peaks in another diffraction pattern.

12. The method of claim 8, wherein comparing the peaks further comprises matching a split peak with a peak having a shoulder as an acceptable match.

13. The method of claims 2 or 5 further comprising
classifying the characteristic peaks by discretely allocating the detected characteristic peaks into one or more groups based on the assigned probability scores.

14. The method of claim 13 wherein the results of the hierarchical cluster analysis are displayed as a dendrogram.

* * * * *